(12) United States Patent
Zhang et al.

(10) Patent No.: US 7,538,202 B2
(45) Date of Patent: May 26, 2009

(54) ENZYME-FREE ISOTHERMAL EXPONENTIAL AMPLIFICATION OF NUCLEIC ACIDS AND NUCLEIC ACID ANALOG SIGNALS

(75) Inventors: David Zhang, Overland Park, KS (US);
Bernard Yurke, Plainfield, NJ (US);
Erik Winfree, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/009,386

(22) Filed: Dec. 9, 2004

(65) Prior Publication Data

US 2005/0227259 A1    Oct. 13, 2005

Related U.S. Application Data

(60) Provisional application No. 60/531,519, filed on Dec. 19, 2003.

(51) Int. Cl.
*C07H 21/04*    (2006.01)
*C12Q 1/68*     (2006.01)

(52) U.S. Cl. ......................................... 536/23.1; 435/6

(58) Field of Classification Search ....................... None
See application file for complete search history.

(56) References Cited

U.S. PATENT DOCUMENTS

| | | | | |
|---|---|---|---|---|
| 5,118,801 | A | * | 6/1992 | Lizardi et al. ............... 536/24.1 |
| 5,914,230 | A | * | 6/1999 | Liu et al. ........................ 435/6 |
| 2004/0053256 | A1 | * | 3/2004 | Lee et al. ........................ 435/6 |

OTHER PUBLICATIONS von Ahsen et al. DNA base bulge vs unmatched end formation in probe-based diagnostic insertion/deletion genotyping: genotyping the UGTIAI (TA)n polymorphism by real-time fluorescence PCR. Clin. Chem. (2000) 46:1939-1945).*

Yurke et al., "A Molecular machine made of and powered by DNA", http://www.bell-labs.com/org/physicalsciences/pubs/yurke01.pdf, 2004, pp. 1-15.

* cited by examiner

*Primary Examiner*—Kenneth R. Horlick
*Assistant Examiner*—David C Thomas
(74) *Attorney, Agent, or Firm*—DLA Piper LLP (US)

(57) ABSTRACT

An enzyme-free, isothermal method of generating an amplification signal indicative of a target nucleic acid molecule is provided, as are compositions for performing such a method. An advantage of the detection system is that it is very sensitive, and can allow for the detection of a single target molecule in a sample.

21 Claims, 6 Drawing Sheets

SEQUENCE LISTING

<160> NUMBER OF SEQ ID NOS: 15

<210> SEQ ID NO 1
<211> LENGTH: 20
<212> TYPE: DNA

```
<213> ORGANISM: Artificial sequence
<220> FEATURE:
<223> OTHER INFORMATION: Synthetic construct

<400> SEQUENCE: 1
atcccatcaa tatcttctca                                                 20

<210> SEQ ID NO 2
<211> LENGTH: 20
<212> TYPE: DNA
<213> ORGANISM: Artificial sequence
<220> FEATURE:
<223> OTHER INFORMATION: Synthetic construct

<400> SEQUENCE: 2
tgagaagata ttgatgggat                                                 20

<210> SEQ ID NO 3
<211> LENGTH: 20
<212> TYPE: DNA
<213> ORGANISM: Artificial sequence
<220> FEATURE:
<223> OTHER INFORMATION: Synthetic construct

<400> SEQUENCE: 3
ctatcataca cactctacta                                                 20

<210> SEQ ID NO 4
<211> LENGTH: 20
<212> TYPE: DNA
<213> ORGANISM: Artificial sequence
<220> FEATURE:
<223> OTHER INFORMATION: Synthetic construct

<400> SEQUENCE: 4
tagtagagtg tgtatgatag                                                 20

<210> SEQ ID NO 5
<211> LENGTH: 20
<212> TYPE: DNA
<213> ORGANISM: Artificial sequence
<220> FEATURE:
<223> OTHER INFORMATION: Synthetic construct

<400> SEQUENCE: 5
ttccactacc tacacatcaa                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic construct

<400> SEQUENCE: 6
ttgatgtgta ggtagtggaa                                                 20

<210> SEQ ID NO 7
<211> LENGTH: 20
<212> TYPE: DNA
<213> ORGANISM: Artificial sequence
<220> FEATURE:
<223> OTHER INFORMATION: Synthetic construct

<400> SEQUENCE: 7
taacctcctc tacaatcctt                                                 20
```

```
<210> SEQ ID NO 8
<211> LENGTH: 20
<212> TYPE: DNA
<213> ORGANISM: Artificial sequence
<220> FEATURE:
<223> OTHER INFORMATION: Synthetic construct

<400> SEQUENCE: 8
aaggattgta gaggaggtta                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic construct

<400> SEQUENCE: 9
aatacttctt cactcaacat                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic construct

<400> SEQUENCE: 10
atgttgagtg aagaagtatt                                              20

<210> SEQ ID NO 11
<211> LENGTH: 20
<212> TYPE: DNA
<213> ORGANISM: Artificial sequence
<220> FEATURE:
<223> OTHER INFORMATION: Synthetic construct

<400> SEQUENCE: 11
tctcctaccc ttcataacta                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic construct

<400> SEQUENCE: 12
tagttatgaa gggtaggaga                                              20

<210> SEQ ID NO 13
<211> LENGTH: 5
<212> TYPE: DNA
<213> ORGANISM: Artificial sequence
<220> FEATURE:
<223> OTHER INFORMATION: Synthetic construct

<400> SEQUENCE: 13 tgaga                                                               5

<210> SEQ ID NO 14
<211> LENGTH: 5
<212> TYPE: DNA
<213> ORGANISM: Artificial sequence
<220> FEATURE:
```

```
<223> OTHER INFORMATION: Synthetic construct

<400> SEQUENCE: 14 ttgat                                                                    5

<210> SEQ ID NO 15
<211> LENGTH: 5
<212> TYPE: DNA
<213> ORGANISM: Artificial sequence
<220> FEATURE:
<223> OTHER INFORMATION: Synthetic construct

<400> SEQUENCE: 15 atgtt                                                                    5
```

ENZYME-FREE ISOTHERMAL EXPONENTIAL AMPLIFICATION OF NUCLEIC ACIDS AND NUCLEIC ACID ANALOG SIGNALS

CROSS REFERENCE TO RELATED APPLICATION(S)

This application claims the benefit of priority under 35 U.S.C. § 119(e) of U.S. Ser. No. 60/531,519, filed Dec. 19, 2003 the entire content of which is incorporated herein by reference.

GRANT INFORMATION

This invention was made with government support under Grant No. EIA-0093486 awarded by the National Science Foundation. The United States government has certain rights in this invention.

BACKGROUND OF THE INVENTION

1. Field of the Invention

The invention relates generally to compositions and methods for detection of a target nucleic acid molecule, and more specifically to compositions and methods for amplifying a signal indicative of a target nucleic acid molecule without the use of enzymes and under isothermal conditions, thus providing for the detection and/or quantitation of a target nucleic acid molecule.

2. Background Information

The polymerase chain reaction (PCR) is the standard molecular biology tool for amplification of DNA molecules. PCR requires a target nucleic acid molecule, a molar excess of forward and reverse primers that bind to the target nucleic acid, deoxyribonucleoside triphosphates (dATP, dCTP, dGTP, and dTTP), and a thermostable DNA polymerase such as Taq polymerase. An amplification reaction is performed under conditions that allow selective hybridization of the forward and reverse primers of an amplification primer pair to the target nucleic acid molecule. Generally, the reaction is performed in a buffered aqueous solution at about pH 7-9.

In a typical PCR amplification cycle, the reaction mixture containing the above is placed in a thermocycler and heated to about 90° C. to 100° C. for about thirty seconds or more. At this temperature the DNA oligonucleotides separate as the hydrogen bonds holding them together break down. The mixture is then cooled down to about 55° C. to about 60° C. At this temperature the forward and reverse primers bind (or anneal) to the single-stranded DNA oligonucleotides. In the final step the mixture is heated again to about 75° C. for at least one minute, which is the optimum temperature for the DNA polymerase enzyme. The polymerase adds bases to the primer segments to build up complementary oligonucleotides of DNA identical to the original molecule. These last three steps can be repeated, for example, up to about thirty times to give about one billion copies of the original DNA. The entire amplification process takes about three hours, with much of the time spent heating and cooling the thermocycler. The amplification products can be detected by standard methods in the art.

There have been many improvements and modification to adapt the original PCR procedure into one that functions as a sensitive detector. However, the nature of most approaches is predominantly biological, as the primary challenges are dependent on the specific properties of the enzymes in question.

Yurke et al., have shown that in the absence of enzymes, DNA are effective fuel-like molecules, and this allows for precise control of movements of DNA in vitro on a nanometer length scale without external prodding (see Yurke et al., "A molecular machine made of and powered by DNA," pp. 115 (2004), on the world wide web (www) at URL "bell-labs.com/org/physicalsciences/pubs/yurk01.pdf"). Yurke et al. focus on DNA processes such as kinetics of branch migrations, kinetic effects of different binding domain lengths, and breathing rates.

Unfortunately, methods and compositions for detection and amplification of nucleic acids which provide the exponential amplification similar to that of PCR, but takes advantage of the kinetics of nucleic acids to drive the reactions without the use of enzymes and under isothermal conditions, has not been described. Thus, a need exists for methods and materials to detect and amplify nucleic acid molecules in the absence of enzymes, using kinetics of nucleic acids and under isothermal conditions.

SUMMARY OF THE INVENTION

The present invention is based, in part, on the development of nucleic acid molecule components that are useful for detecting a target nucleic acid molecule in a sample. In particular, the nucleic acid components of the invention allow for the generation of a signal that is indicative of the presence of the target nucleic acid molecule by providing an amplification system that functions under isothermal conditions and does not require enzymes or other protein components. A further advantage of the nucleic acid components of the invention is that they permit stoichiometric conversion of a target nucleic acid molecule to a signal, thus allowing for a quantitative determination of the amount of a target nucleic acid in a sample. Accordingly, the present invention provides compositions, including target nucleic acid molecule translator components and amplifier nucleic acid components, systems comprising such components, and methods of using the components and systems to identify and/or quantitate a target nucleic acid molecule in a sample.

In one embodiment, the present invention relates to amplifier nucleic acid molecules, each of which comprises a damping oligonucleotide and one or more propagating oligonucleotides. In various aspects, an amplifier nucleic acid molecule of the invention comprises a complex of a damping oligonucleotide and one propagating oligonucleotide (a "gain1" component), a complex of a damping oligonucleotide and two propagating oligonucleotides (a "gain2" component), a complex of a damping oligonucleotide and three propagating oligonucleotides (a "gain3" component), etc. A damping oligonucleotide includes a toehold domain, to which an exogenous polynucleotide can selectively hybridize, and sets of two, four, six, or more propagating oligonucleotide binding domains. The exogenous polynucleotide that can selectively hybridize to a toehold domain can be, for example, an exogenous propagating oligonucleotide (i.e., a propagating oligonucleotide that is not otherwise part of the amplifier nucleic acid molecule comprising the damping oligonucleotide toehold).

A propagating oligonucleotide includes domains that are complementary to and can selectively hybridize to two or more domains of a damping oligonucleotide, including, in an amplifier nucleic acid molecule, domains that hybridize only to the propagating oligonucleotide binding domains on the damping oligonucleotide. Upon hybridizing to a damping oligonucleotide to form an amplifier nucleic acid molecule, the propagating oligonucleotide comprises a loop (bulge)

region. In comparison, an exogenous propagating oligonucleotide that can selectively hybridize to a toehold domain of a damping oligonucleotide generally is substantially complementary to a target damping oligonucleotide over its full length, and can branch migrate to form a two oligonucleotide complex (i.e., a double stranded molecule). The exogenous propagating oligonucleotide, by branch migration and hybridization to a damping oligonucleotide of an amplifier nucleic acid molecule, can displace one or more propagating oligonucleotide(s).

An amplifier nucleic acid molecule of the invention is exemplified by amplifier nucleic acid molecule 1, which contains a first damping oligonucleotide 10 (also referred to herein as "D1") and at least one (e.g., 1, 2, 3, 4, or more) first propagating oligonucleotide 40 (also referred to herein as "P2"). In one aspect, the first damping oligonucleotide 10 includes, in operative linkage in a 5' to 3' orientation, a first toehold domain 210 of at least two nucleotides (e.g., 2, 3, 4, 5, 6, 7, 8, 9, 10, or more), and at least two first propagating oligonucleotide binding domains 230 and 240, each of binding domains 230 and 240 comprising at least six nucleotides (e.g., 6, 7, 8, 9, 10, 11, 12, or more). The first propagating oligonucleotide 40 (P2) includes, in operative linkage in a 3' to 5' orientation, a first domain 130, which is complementary to and selectively hybridizes the first propagating oligonucleotide binding domain 230, at least two (i.e., one set of) domains 150 and 160, which are not complementary to the first damping oligonucleotide 10, each of domains 150 and 160, comprising at least six nucleotides, and a sixth domain 140, which is complementary to and selectively hybridizes to the first propagating oligonucleotide binding domain 240. In another aspect, the toehold domain as at the 3' terminus of the damping oligonucleotide, with a corresponding modification in the appropriate propagating oligonucleotide of a nucleic acid amplification system as disclosed herein. As will be apparent, in a gain1 component, a damping oligonucleotide (e.g., D1) contains one set of propagating oligonucleotide binding domains 230 and 240 and the corresponding propagating oligonucleotide (e.g., P2) contains two domains 150 and 160, which are not complementary to the damping oligonucleotide; in a gain2 component, a damping oligonucleotide (e.g., D1) contains two sets of propagating oligonucleotide binding domains 230, 240, 230 and 240 and the corresponding propagating oligonucleotide (e.g., P2) contains four domains 150, 160, 150 and 160, which are not complementary to the damping oligonucleotide; etc.

Accordingly, in one aspect, the damping oligonucleotide 10 of the amplifier nucleic acid molecule 1 contains two first propagating oligonucleotide binding domains 230 and 240, wherein, upon hybridization of a first propagating oligonucleotide 40 comprising domains 150 and 160, a complex comprising the first damping oligonucleotide 10 and the first propagating oligonucleotide 40 (a gain1 component; P2*D1) is formed. In another aspect, the damping oligonucleotide 10 of the amplifier nucleic acid molecule 1 contains four first propagating oligonucleotide binding domains 230, 240, 230 and 240, wherein, upon hybridization of two first propagating oligonucleotides 40 comprising domains 150, 160, 150 and 160, a complex comprising the first damping oligonucleotide 10 and the two first propagating oligonucleotides 40 (a gain2 component; ($P2_2$*D1) is formed. In still another aspect, the first damping oligonucleotide 10 of the amplifier nucleic acid molecule 1 contains six first propagating oligonucleotide binding domains 230, 240, 230, 240, 230, and 240, wherein, upon hybridization of three first propagating oligonucleotides 40 comprising domains 150, 160, 150, 160, 150 and 160, a complex comprising the first damping oligonucleotide 10 and the three first propagating oligonucleotides 40 (a gain3 component; $P2_3$*D1) is formed. Similarly, gain4 ($P2_4$*D1), gain5 ($P2_5$*D1), etc. components are provided.

Additional amplifier nucleic acid molecules are exemplified herein by a second amplifier nucleic acid molecule 2 and a third amplifier nucleic acid molecule 3. The second amplifier nucleic acid molecule 2 includes a second damping oligonucleotide 30 ("D2") and at least one second propagating oligonucleotide 60 ("P3"). An exemplary second amplifier nucleic acid molecule 2 ($P3_2$*D2) includes the second damping oligonucleotide 30 (D2), which contains, in operative linkage in a 5' to 3' orientation, a first toehold domain 230 comprising at least two nucleotides, and at least four second propagating oligonucleotide binding domains 250, 260, 250, and 260, each of which comprises at least six nucleotides. As will be apparent, the second damping oligonucleotide 30 (D2) is substantially complementary and can selectively hybridize to the first propagating oligonucleotide 40 (P2). The second amplifier nucleic acid molecule 2 ($P3_2$*D2) also includes two second propagating oligonucleotides 60 (P3), each of which contains, in operative linkage in a 3' to 5' orientation, a first domain 150, which is complementary to and selectively hybridizes to the second propagating oligonucleotide binding domain 250, at least four domains 110, 120, 110, and 120, which are not complementary to the second damping oligonucleotide 30, each of domains 110, 120, 110, and 120 comprising at least six nucleotides, and a sixth domain 160, which is complementary to and selectively hybridizes to the second propagating oligonucleotide binding domain 260. As such, the amplifier nucleic acid molecule 2 comprises a complex that includes the second damping oligonucleotide 30 and the two second propagating oligonucleotides 60 (i.e., a $P3_2$*D2 complex).

The third amplifier nucleic acid molecule 3 includes a third damping oligonucleotide 50 ("D3") and at least one third propagating oligonucleotide 20 ("P1"). An exemplary third amplifier nucleic acid molecule 3 ($P1_2$*D3) includes the third damping oligonucleotide 50, which contains, in operative linkage in a 5' to 3' orientation, a first toehold domain 250 comprising at least two nucleotides, and at least four second propagating oligonucleotide binding domains 210, 220, 210, and 220, each of which comprises at least six nucleotides. As will be apparent, the third damping oligonucleotide 50 (D3) is substantially complementary and can selectively hybridize to the second propagating oligonucleotide 60 (P3). The third amplifier nucleic acid molecule 3 also includes two third propagating oligonucleotides 20 (P1) each of which contains, in operative linkage in a 3' to 5' orientation, a first domain 110, which is complementary to and selectively hybridizes to the second propagating oligonucleotide binding domain 210, at least four domains 130, 140, 130, and 140, which are not substantially complementary to the second damping oligonucleotide 50, each of domains 130, 140, 130, and 140 comprising at least six nucleotides, and a sixth domain 120, which is complementary to and selectively hybridizes to the second propagating oligonucleotide binding domain 220. As such, the amplifier nucleic acid molecule 3 is a complex of the third damping oligonucleotide 50 and the two third propagating oligonucleotides 20 (i.e., a $P1_2$*D3 complex). Further, as will be apparent, the third propagating oligonucleotide 20 (P1) is substantially complementary to and can selectively hybridize to the first damping oligonucleotide 10 (D1) of amplifier nucleic acid molecule 2. As such, amplifier nucleic acid molecule 1, amplifier nucleic acid molecule 2, and amplifier nucleic acid molecule 3, each comprising a complex of one damping oligonucleotide and two propagating oligonucleotides, can be represented by ($P2_2$*D1, $P3_2$*D2, and $P1_2$*D3), respectively.

In addition to the domains referred to above, a damping oligonucleotide and/or a propagating oligonucleotide can contain one or more additional domains (nucleotide sequences). As such, the first damping oligonucleotide 10, for example, can further include a nucleotide sequence domain 205 positioned 5' to the toehold domain or positioned between the toehold domain 210 and the first propagating oligonucleotide binding domains 230 and 240; or can further contain a nucleotide sequence domain 225 positioned between the first propagating oligonucleotide binding domains 230 and 240; or can further contain a 3' terminal nucleotide sequence domain 220, or can contain any other domain, or combinations of such domains. Similarly, propagating oligonucleotide 40, for example, also can contain one or more additional domains. It will be recognized, however, that specific relationships exist among propagating oligonucleotides and damping oligonucleotides of an amplifier nucleic acid molecule, and particularly among amplifier nucleic acid molecules of a nucleic acid amplification system as disclosed herein and, therefore, that the inclusion of such additional domains is subject to certain constraints.

The propagating oligonucleotide binding domain of a damping oligonucleotide is at least six nucleotides in length, thus allowing selective hybridization of a propagating oligonucleotide to the set of binding domains, for example, hybridization of first domain 130 and sixth domain 140 of the first propagating oligonucleotide 40 to propagating oligonucleotide binding domains 230 and 240 of the first damping oligonucleotide 10. A binding domain can contain any number of nucleotides greater than six, with an upper limit generally being selected based, for example, on the convenience of preparing the various oligonucleotides, as well as the time it will take for hybridization and branch migration to proceed in the methods for which the compositions are used. As such, a propagating oligonucleotide binding domain generally is at least about 6 nucleotides in length, and can range from about 6 nucleotides to about 100 nucleotides (e.g., 5, 6, 7, 8, 9, 10, 12, 14, 16, 18, 20, 25, 30, 40, 50, 75, or 100).

The toehold domain of a damping oligonucleotide is at least about two nucleotides in length (i.e. 2, 3, 4, 5, 6, 7, 8, etc.) such that an exogenous nucleic acid molecule, for example, a target nucleic acid molecule or a propagating oligonucleotide of an amplifier nucleic acid molecule other than that comprising the toehold domain can selectively hybridize such that branch migration can occur. In one aspect, the toehold domain, for example, the first toehold domain 210 of the damping oligonucleotide 10 is at least two nucleotides in length. In another aspect, the toehold is at least five nucleotides in length.

An amplifier nucleic acid molecule of the invention can contain a label, which conveniently provides a means to determine, for example, whether the amplifier nucleic acid molecule comprises a complex, or whether the complex has been dissociated (e.g., whether one or more propagating oligonucleotides has been displaced from the damping oligonucleotide). The label can be any moiety or moieties of interest, including, for example, a fluorescent label, a luminescent label, chemiluminescent label, a colorigenic label, a radionuclide, or a paramagnetic label. In one aspect, the label comprises a fluorescence resonance energy transfer (FRET) pair, including a first fluorescent label and second fluorescent label with overlapping emission and excitation spectra, respectively; or a fluorescent label and a fluorescence quencher that quenches the fluorescence of the fluorescent label. By providing the FRET pair in appropriate proximity in the amplifier nucleic acid molecule, dissociation of the complex can be detected by detecting FRET, which can be a shift in a fluorescence spectrum where the FRET pair comprises two fluorescent labels, or can be an increase in fluorescence where the FRET pair comprises a fluorescent label and a quencher.

The damping oligonucleotide and or propagating oligonucleotide(s) of a nucleic acid amplifier (or translator component, see below) can comprise DNA or RNA molecules, or a combination thereof, and further can include naturally and/or non-naturally occurring nucleotides, which can be linked by phosphodiester and/or other (e.g., peptide, phosphothioester) bonds. Such modified oligonucleotides can provide the advantage that the compositions (e.g., amplifier nucleic acid molecules) can be more resistant to degradation by nucleases that may be present in a reaction containing the oligonucleotides, and more stable to long term storage.

In various embodiments, the amplifier nucleic acid molecules of the invention (e.g., gain2 amplifier nucleic acid molecules) are useful in a 1 cycle, 2 cycle, or a 3 cycle amplification reactions, or more. A 1 cycle amplification system is substantially as described above. A 2 cycle amplification reaction requires two different amplifier nucleic acid molecules (e.g., $P2_2$*D1 and $P1_2$*D2), wherein, in the first cycle, a "free" (e.g., displaced) P2 of the first amplifier nucleic acid molecule can selectively hybridize to the toehold domain of D2 of the second amplifier nucleic acid molecule, and displace, by branch migration, the two P1 oligonucleotides of the second amplifier molecule, which, in the second cycle, can selectively hybridize to the toehold domains of intact first amplifier nucleic acid molecules, thereby maintaining the 2 cycle amplification reaction.

An example of an amplifier nucleic acid molecule useful in a 2 cycle amplification reaction is provided by gain2 amplifier nucleic acid molecule 1 ($P2_2$*D1), which includes a first damping oligonucleotide 10, which comprises, in operative linkage in a 5' to 3' orientation, a first toehold domain 210 comprising at least two nucleotides, and four first propagating oligonucleotide binding domains 230, 240, 230 and 240, each of binding domains 230, 240, 230 and 240 comprising at least six nucleotides; and two first propagating oligonucleotides 40, each of which comprises, in operative linkage in a 3' to 5' orientation, a first domain 130, which is complementary to and selectively hybridizes to the first propagating oligonucleotide binding domain 230, at least two domains 150 and 160, which are not complementary to the first damping oligonucleotide 10, each of domains 150 and 160 comprising at least six nucleotides, and a fourth domain 140, which is complementary to and selectively hybridizes to a nucleotide sequence of the first propagating oligonucleotide binding domain 240 of the damping oligonucleotide 10. The first damping oligonucleotide 10 of such a gain2 amplifier nucleic acid molecule 1 can further include a 3' terminal nucleotide sequence domain 220. Similarly, a gain2 amplifier nucleic acid molecule 2 ($P1_2$*D2) useful in a 2 cycle amplification also is provided.

In comparison to a 2 cycle amplification reaction, a 3 cycle amplification reaction requires three different amplifier nucleic acid molecules (e.g., $P2_2$*D1, $P3_2$*D2, and $P1_2$*D3), wherein, in the first cycle, each of the two displaced P2 oligonucleotides of the first amplifier nucleic acid molecule can selectively hybridize to the toehold domains of two D2 oligonucleotides of second amplifier nucleic acid molecules and displace, by branch migration, each of the two P3 oligonucleotides of the second amplifier molecules (4 total), each of which, in the second cycle, can selectively hybridize to the toehold domain of four D3 oligonucleotides of third amplifier nucleic acid molecules and displace, by branch migration each of the two P1 oligonucleotides (8 total), each of which, in the third cycle, can selectively hybridize to the toehold domains of eight intact first amplifier nucleic acid molecules, thereby maintaining the 3 cycle reaction.

An example of an amplifier nucleic acid molecule useful in a 3 cycle amplification reaction is provided by gain2 amplifier nucleic acid 1 ($P2_2*D1$) as disclosed above (e.g., a gain2 amplifier nucleic acid molecule 1 comprising a first damping oligonucleotide 10 and two first propagating oligonucleotides 40). The first damping oligonucleotide 10 of such a gain2 amplifier nucleic acid molecule 1 can further include a 3' terminal nucleotide sequence domain 220. Similarly, a gain2 amplifier nucleic acid molecule 2 ($P3_2*D2$) and a gain2 amplifier nucleic acid molecule 3 ($P1_2*D3$) useful in a 3 cycle amplification are provided.

The present invention also relates to compositions containing one or more amplifier nucleic acid molecules of the invention. In one embodiment, the composition includes an amplifier nucleic acid molecule and a restriction oligonucleotide, which can selectively bind to a propagating oligonucleotide binding domain of a damping oligonucleotide, but, if displaced, cannot propagate an amplification cycle. Such a composition is exemplified by amplifier nucleic acid molecule in FIG. 6, whereby the damping oligonucleotide (D1) is hybridized to one propagating oligonucleotide (P2) and a restriction oligonucleotide that includes, operatively linked and in a 3' to 5' orientation, a first domain 130, a seventh domain, which is not complementary to damping oligonucleotide 10 (e.g., a poly-thymidine sequence) and a sixth domain 140, wherein the restriction oligonucleotide selectively hybridizes to the damping oligonucleotide. Similar restriction oligonucleotide compositions for amplifier nucleic acid molecule 2 and/or an amplifier nucleic acid molecule 3, or combinations of such amplifier nucleic acid molecules and restriction oligonucleotides also are provided.

In another embodiment, a composition of the invention includes an amplifier nucleic acid molecule and a propagating oligonucleotide that can selectively hybridize to the damping oligonucleotide of the amplifier nucleic acid molecule. Such a composition is exemplified by a composition that includes amplifier nucleic acid molecule 1 ($P2_2*D1$), and second propagating oligonucleotide 20 (P1), which includes, in operative linkage in a 3' to 5' orientation, a first domain 110, second domain 130, third domain 140, fourth domain 130, fifth domain 140, and sixth domain 120. Similarly, compositions that include, for example, $P3_2*D2$ and $P2_2*D1$, or $P1_2*D3$, or combinations thereof, also are provided. As will be apparent, a characteristic of the present compositions is that various oligonucleotides are substantially complementary to other oligonucleotides; for example, a first damping oligonucleotide (D1) is substantially complementary to a first propagating oligonucleotide (P1). As such, where a damping oligonucleotide (e.g., D1) comprises a toehold domain at the 3' terminus (as compared to the exemplified damping oligonucleotides, which contain the toehold domain at the 5' terminus), the corresponding propagating oligonucleotide (e.g., P1) similarly must be modified so as to maintain the substantial complementarity.

As used herein, the term "substantially complementary" means that a first oligonucleotide (e.g., a P1) shares sufficient complementarity with a second (or third, fourth, or other oligonucleotide; e.g., a D1) such that, upon binding of the first and second oligonucleotides via a toehold, branch migration can occur such that the first and second oligonucleotides form a double stranded nucleic acid molecule (a P1/D1 complex). A functional characteristic of substantially complementary oligonucleotides (e.g., P1 and D1) is that, upon hybridization, they form a relatively stable duplex nucleic acid molecule under conditions of an amplification method of the present invention. Generally, a first and substantially complementary second oligonucleotide are at least about 70% identical over the region that selectively hybridizes (e.g., 70%, 75%, 80%, 85%, 90%, 95%, 98%, 99% or 100%), although the first (or other) oligonucleotide can contain, for example, a 5' and/or 3' region that is not necessarily complementary with the other (or first) oligonucleotide, respectively. For example, in a duplex of P1, which is 120 nucleotides in length, and D1, which is 85 nucleotides in length, P1 is bound to D1 at 85 of 120 nucleotides (70.8%), whereas D1 is bound to P1 at all 85 of its (D1) nucleotides (100%).

The present invention also relates to target nucleic acid molecule translator system ("translator"), which, when contacted with a target nucleic acid molecule, provides a propagating oligonucleotide that can initiate an amplification reaction utilizing amplifier nucleic acid molecules of the invention. A translator of the invention is exemplified by first gain1 component 4, which contains a toehold complementary to the target nucleic acid molecule, and a second gain1 component 5, which provides a propagating oligonucleotide (P1) that, when displaced from the second gain1 component 5, can initiate an amplification reaction.

The first gain1 component 4 of a translator includes a fourth damping oligonucleotide 70 and a fourth propagating oligonucleotide 80. The fourth damping oligonucleotide 70 contains, in operative linkage in 5' to 3' direction, a first toehold domain 26, which comprises at least two nucleotides and is complementary to and selectively hybridizes to a 3' nucleotide sequence of the target nucleic acid molecule; two fourth propagating oligonucleotide binding domains 280 and 290, each comprising at least six nucleotides; and, optionally, a fourth domain which is complementary to and hybridizes to a 5' nucleotide sequence of the target nucleic acid molecule. The fourth propagating oligonucleotide 80 contains, in operative linkage in a 3' to 5' orientation, a first domain 180, which is complementary to and selectively hybridizes to the fourth propagating oligonucleotide binding domain 280, two domains 110 and 120, which are not complementary to the fourth damping oligonucleotide 70, each of domains 110 and 120 comprising at least six nucleotides, and a fourth domain 190, which is complementary to and selectively hybridizes to the fourth propagating oligonucleotide binding domain 290. As such, the first gain1 component 4 comprises a complex of the fourth damping oligonucleotide 70 and the fourth propagating oligonucleotide 80. Further, there can exist 3' toehold domain 26, alone, or together with the 5' toehold domain, which comprises at least two nucleotides and is complementary to and selectively hybridizes to a 5' nucleotide sequence of the target nucleic acid molecule.

The second gain1 component 5 of the translator includes a fifth damping oligonucleotide 90 and a third propagating oligonucleotide 20 (e.g., P1). The fifth damping oligonucleotide 90, contains, in operative linkage in a 5' to 3' orientation, a first toehold domain 280, which is complementary to and selectively hybridizes to the first domain 180 of the fourth propagating oligonucleotide 80, two third propagating oligonucleotide binding domains 210 and 220, each comprising at least six nucleotides, and a fourth domain 290. As will be apparent, the fifth damping oligonucleotide 90 is substantially complementary to and can selectively hybridize to the fourth propagating oligonucleotide 80 of the first gain1 component 4. In the present example, the third propagating oligonucleotide 20 (initiator) corresponds to P1 as described above, and contains, in operative linkage in a 3' to 5' orientation, a first domain 110, which is complementary to and selectively hybridizes to third propagating oligonucleotide binding domain 210, at least four domains 130, 140, 130, and 140, which are not complementary to the fifth damping oligonucleotide 90, each of domains 130, 140, 130, and 140 comprising at least six nucleotides, and a sixth domain 120, which is complementary to and selectively hybridizes to third propagating oligonucleotide binding domain 220, wherein the second gain1 component 5 comprises a complex of the fifth damping oligonucleotide 90 and the third propagating oligonucleotide 20. As will be apparent, upon displacement of the third propagating oligonucleotide 20 (P1) from the second gain1 component 5, the third propagating oligonucleotide (P1) can selectively bind to the toehold domain of a $P2_2*D1$ amplifier nucleic acid molecule 1 and thereby initiate a nucleic acid amplification reaction.

Accordingly, the present invention further relates to a nucleic acid amplification system, which provides a means to detect and/or quantitate a target nucleic acid molecule. A nucleic acid amplification system can be a 2 cycle system, a 3 cycle system, etc. A 3 cycle nucleic acid amplification system can be exemplified by the first amplifier nucleic acid amplifier 1, second amplifier nucleic acid molecule 2, and third amplifier nucleic acid molecule 3, as described above. Such a nucleic acid amplification system can further include a target nucleic acid molecule translator system. In one embodiment, the nucleic acid amplification system is provided as a kit, wherein the amplifier nucleic acid molecules are included separately or as a mixture. Further, the kit can contain one or a plurality of translator systems or first and second gain1 components of the translator system(s). For example, the kit can contain a plurality of different first gain1 translator system components, each different component having a toehold domain for different target nucleic acid molecules (e.g., each of a family of related target molecules, or each of a normal and a mutant target molecule). The second gain1 translator system component can be the same when included with a plurality of different first gain1 translator system components.

One or more of amplifier nucleic acid molecule 1, the amplifier nucleic acid molecule 2, and the amplifier nucleic acid molecule 3 of the exemplified nucleic acid amplification system can further include a label. In one embodiment, one or more amplifier nucleic acid molecules of the system comprises a fluorescence resonance energy transfer (FRET) pair. In one aspect of this embodiment, the FRET pair includes a fluorescent label and a fluorescence quencher, wherein, in an amplifier nucleic acid molecule comprising a complex of a damping oligonucleotide and a propagating oligonucleotide, the fluorescence quencher quenches fluorescence of the fluorescent label, and wherein, upon dissociation of the damping oligonucleotide and the propagating oligonucleotide of the amplifier nucleic acid molecule, fluorescence of the fluorescent label is not quenched, thus providing a means to detect displacement of the propagating oligonucleotide(s) and, therefore, the presence of a target nucleic acid molecule.

The present invention also relates to a method of identifying a target nucleic acid molecule in a sample. Such a method can be performed, for example, by contacting, under conditions suitable for selective hybridization of the target nucleic acid molecule to the toehold domain of the first gain1 component of the translator, at least one sample with a nucleic acid amplification system comprising a translator and amplifier nucleic acid molecules and detecting dissociation of one or more propagating oligonucleotide(s) of one or more amplifier(s). For example, referring to the above-described nucleic acid amplification comprising a translator and three amplifier nucleic acid molecules, the target nucleic acid molecule can selectively hybridize to the first toehold domain 26 of the damping oligonucleotide 70 of the first gain1 component 4 of the target nucleic acid molecule translator system, and dissociation of the first propagating oligonucleotide 40 from the amplifier nucleic acid molecule 1, the second propagating oligonucleotide 40 from the amplifier nucleic acid molecule 2, and/or the third propagating oligonucleotide 20 from the amplifier nucleic acid molecule 3 can be detected. According to this method, increased dissociation of the propagating oligonucleotide from the amplifier nucleic acid molecule in the presence of the target nucleic acid molecule as compared to the absence of the target nucleic acid molecule is indicative of the presence of a target nucleic acid molecule, thereby identifying the target nucleic acid molecule in the sample.

A target nucleic acid molecule can be any nucleic acid molecule, including a deoxyribonucleic acid molecule (DNA) or a ribonucleic acid molecule (RNA). The sample can be any sample that contains or is suspected of containing a target nucleic acid molecule, including, for example, a biological sample or an environmental sample. In one embodiment, the sample comprises a cell sample (e.g., a human cell sample), which can be a sample of cells of a cell culture (e.g., an established cell line or cells obtained from a living subject and maintained in culture) or can be a sample of cells obtained from a subject (e.g., a biopsy sample). As such, the present methods can be used to examine a sample of cells from a subject in order to identify an abnormal condition (e.g., an infection, a cancer, a congenital disorder, or susceptibility to a cancer or congenital disorder), can be used to identify a biological contaminant in an environmental sample, can be used for forensic purposes (e.g., to examine a blood, semen, or other biological sample at a crime scene), and the like.

The target nucleic acid molecule can be any nucleic acid molecule of interest, including DNA and/or RNA, and can be identified, for example, based on the presence (or absence) of a mutation or a polymorphism (e.g., a single nucleotide polymorphism (SNP). For example, by designing a toehold domain of the first gain1 component of a translator such that a mutant nucleotide sequence of a target nucleic acid, but not the corresponding sequence of the normal gene (i.e., not containing the mutation), can selectively hybridize, detection of dissociated propagating oligonucleotides of amplifier nucleic acid molecules is indicative of the presence of the mutant target nucleic acid molecule. The target nucleic acid molecule also can be an oncogene or a tumor suppressor gene, can be a plant nucleic acid molecule, a bacterial nucleic acid molecule (e.g., to determine whether an individual has an infection, or whether an infecting bacterium has a gene that may be susceptible (or resistant) to a particular antibiotic), or a viral nucleic acid molecule (e.g., to identify or confirm the presence of a viral infection), or can be an mRNA molecule (e.g., to detect expression, or lack thereof, of a particular gene, such as in response to an agent being tested to determine whether it can effect regulation of the gene). A target nucleic acid molecule also can be, for example, a cDNA molecule, a small interfering RNA molecule (siRNA, RNAi), and/or an aptamer.

The method of identifying a target nucleic acid molecule in a sample can further include a step of quantitating the amount of target molecule in the sample. Quantitation of the target molecule is possible because the method can be performed such that dissociation of the propagating oligonucleotide from the nucleic acid amplifier molecule is stoichiometric with respect to the target nucleic acid molecule in the sample (e.g., dissociation of the propagating oligonucleotide can occur in a 1:1 ratio to the amount of the target nucleic acid molecule in the sample, or in a 2:1 ratio, or more (e.g., in an 8:1 ratio)).

The methods of the invention can be performed on a solid support such as a glass slide, a bead, or a silicon wafer, and/or can be performed using a microfluidic device. Further, the methods conveniently can be adapted to a high throughput format, which can, but need not, be automated (or semi-automated), and can allow for the examination of a plurality of samples, which can be the same (e.g., duplicates, triplicates, etc., to increase statistical validity of results) or different (e.g., samples from different subjects, or from different tissues or organs of a single subject, or combinations thereof, and control samples). A plurality of samples can be positioned on a solid support, including in wells or pits of a solid support, and can be arranged in an array, which can be an addressable array, thus facilitating the addition or removal of reagents and analysis of the reaction results.

The present invention further relates to a method of identifying an agent that effects expression of a target nucleic acid molecule. Such a method can be performed, for example, by contacting a sample comprising the target nucleic acid molecule with a test agent under conditions suitable for effecting expression of the target nucleic acid molecule; further contacting the sample with a nucleic acid amplification system of the invention, under conditions suitable for selective hybridization of the target nucleic acid molecule to the first toehold domain of the damping oligonucleotide of the first gain1 component of the target nucleic acid molecule translator system, and detecting dissociation of propagating oligonucleotides from the amplifier nucleic acid molecule(s), wherein a change in dissociation of the propagating oligonucleotide(s) from the amplifier nucleic acid molecule(s) in the presence of the test agent as compared to the absence of the test agent identifies the test agent as an agent that effects expression of the target nucleic acid molecule.

The method of identifying an agent that effects expression of a target nucleic acid molecule can be performed in a high throughput format, thus allowing for the examination of a number of samples and/or number of test agents in parallel. The test agent can be any molecule, including, for example, a polynucleotide, peptide, peptidomimetic, small organic molecule (e.g., an aptamer or a DNA binding protein, or DNA binding domain of such a protein) that has or is suspected of having target molecule expression effecting activity, and can be a test agent of a plurality of test agents (e.g., a combinatorial library of test agents, which can be a random library of test agents, a biased library of test agents, a variegated library of test agents, or a combination thereof).

The sample containing the target nucleic acid molecule can be any sample, including, for example, a cell sample (e.g., a viral, bacterial, plant, or animal cell sample). Further, the sample can be contacted with the test agent in vitro or in vivo (e.g., by administering the test agent to a subject, then collecting a cell sample), then can be examined using a nucleic acid amplification system of the invention. Accordingly, the invention also provides an agent identified by such a method.

The present invention also relates to a method of translating a target nucleic acid molecule into a propagating oligonucleotide, which can initiate amplification of a nucleic acid amplification system under isothermal conditions. Such a method can be performed, for example, by contacting a sample comprising a target nucleic acid molecule with a target nucleic acid molecule translator under conditions suitable for selective hybridization of the target nucleic acid molecule to the toehold domain of the damping oligonucleotide of the first gain1 component of the translator, wherein the target nucleic acid molecule hybridizes to the damping oligonucleotide by branch migration and displaces the propagating oligonucleotide from the first gain1 component, thereby generating a dissociated propagating oligonucleotide that can selectively hybridize to the toehold domain of the damping oligonucleotide of the second gain1 component, wherein the dissociated propagating oligonucleotide displaces, by branch migration, the propagating oligonucleotide of the second gain1 component (i.e., the initiator), thereby displacing a propagating oligonucleotide that can initiate amplification of a nucleic acid amplification system under isothermal conditions. In one embodiment, dissociation (displacement) of the initiator propagating oligonucleotide(s) is stoichiometric with respect to the target nucleic acid molecule in the sample (e.g., the initiator is generated in a 1:1 ratio to the amount of the target nucleic acid molecule in the sample, or in 2:1 ratio, etc.).

The method of translating a target nucleic acid molecule into a propagating oligonucleotide, which can initiate amplification of a nucleic acid amplification system under isothermal conditions, can further include initiating amplification of a nucleic acid amplification system. Such a method can be performed, for example, by contacting, under isothermal conditions, a target nucleic acid molecule and the target nucleic acid molecule translator with the nucleic acid amplification system as disclosed herein, whereby the dissociated initiator propagating oligonucleotide from the second gain1 translator component selectively hybridizes to the toehold domain of a first damping oligonucleotide of an amplifier nucleic acid molecule of the system, thereby initiating amplification.

BRIEF DESCRIPTION OF THE DRAWINGS

FIG. 1A shows a sample containing target nucleic acid molecules. FIG. 1B shows a translator nucleic acid molecule, which is contacted with the test sample. FIG. 1C shows an amplification system containing three gain2 amplifier nucleic acid molecules. FIG. 1D shows a detection system that includes a spectrophotometer.

DETAILED DESCRIPTION OF THE INVENTION

Figure 1:
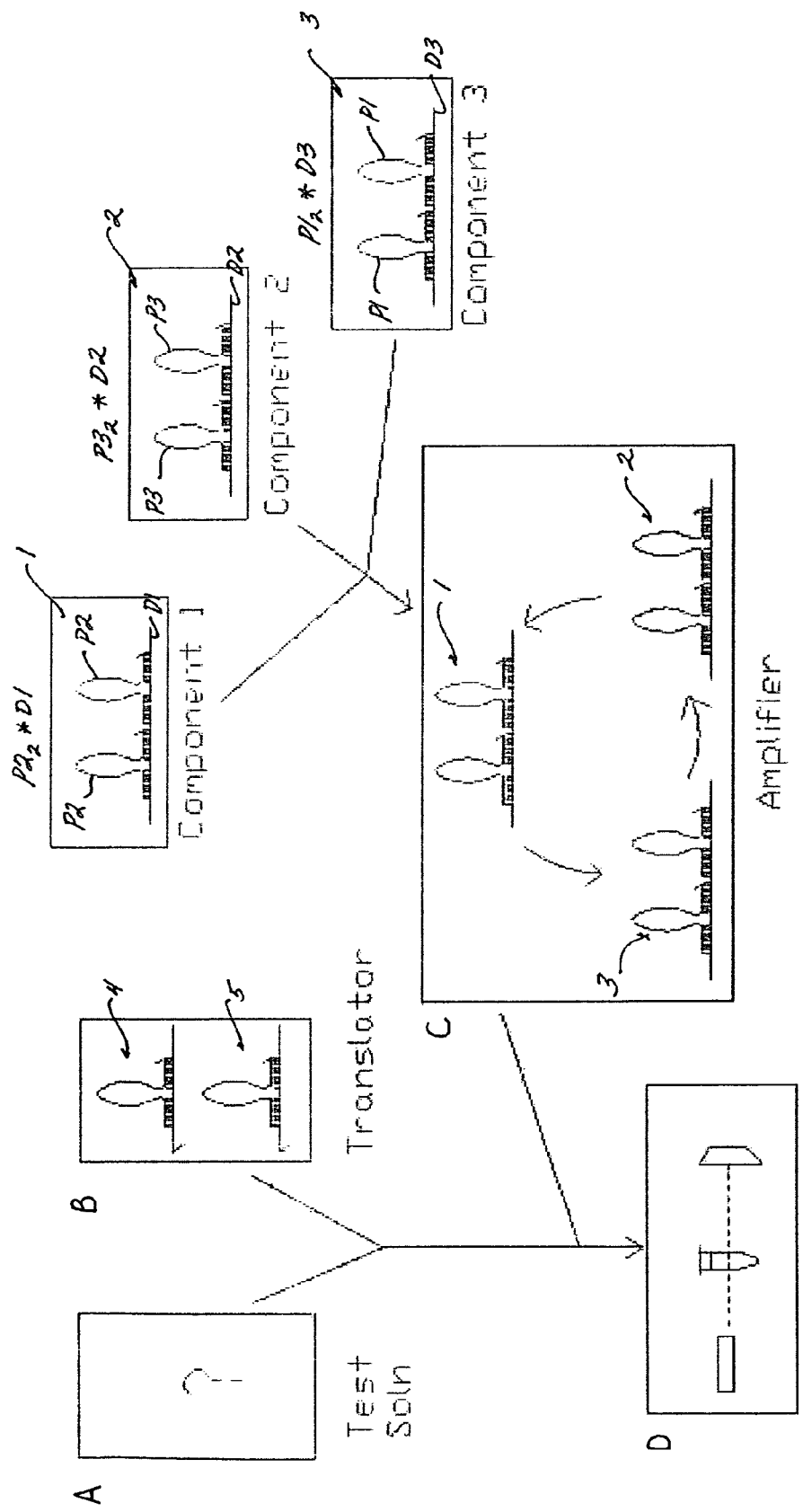
FIGS. 1A to 1D show a systems diagram of the enzymatic-free nucleic acid detection and amplification system.

The present invention provides compositions and methods for performing an amplification reaction that allows for the detection of a target nucleic acid molecule (target sequence). An advantage of the compositions and methods is that that amplification reaction(s) proceed in the absence of enzymes and under isothermal conditions. As such, the invention provides various nucleic acid molecules, including oligonucleotides, which function in the detection of a target nucleic acid molecule and generation of a signal indicative of the target molecule. As a further advantage, the compositions and methods allow for the stoichiometric conversion of a target sequence to a signal, thus providing quantitation of the target nucleic acid molecule.

The compositions of the invention generally include free and/or complexed oligonucleotides, including, for example, propagating oligonucleotides and damping oligonucleotides. The term "oligonucleotide" is used broadly herein to mean a sequence of two or more deoxyribonucleotides or ribonucleotides that are linked together by a phosphodiester bond. As such, oligonucleotide(s) includes RNA and DNA, which can be a gene or a portion thereof, a cDNA, a synthetic polydeoxyribonucleic acid sequence, or the like, and can be single oligonucleotide or double oligonucleotides, as well as a DNA/RNA hybrid. Furthermore, as used herein, "oligonucleotide" includes naturally occurring nucleic acid molecules, which can be isolated from a cell, as well as synthetic molecules, which can be prepared, for example, by methods of chemical synthesis or by enzymatic methods. In various embodiments, a polynucleotide of the invention contains nucleoside or nucleotide analogs, and/or backbone bonds other than a phosphodiester bond.

In general, the nucleotides comprising an oligonucleotide are naturally occurring deoxyribonucleotides, such as adenine, cytosine, guanine or thymine linked to 2'-deoxyribose, or ribonucleotides such as adenine, cytosine, guanine or uracil linked to ribose. However, an oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234 (1994); Jellinek et al., *Biochemistry* 34:11363-11372 (1995); Pagratis et al., *Nature Biotechnol.* 15:68-73 (1997), each of which is incorporated herein by reference).

The covalent bond linking the nucleotides of a oligonucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., Nucl. Acids Res. 22:977-986 (1994); Ecker and Crooke, *BioTechnology* 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

Moreover, oligonucleotides of the present invention, comprising naturally occurring nucleotides and phosphodiester bonds can be chemically synthesized or can be produced using recombinant DNA methods, using an appropriate polynucleotide as a template. In comparison, an oligonucleotide comprising nucleotide analogs or covalent bonds other than phosphodiester bonds generally will be chemically synthesized, although an enzyme such as T7 polymerase can incorporate certain types of nucleotide analogs into an oligonucleotide and, therefore, can be used to produce such an oligonucleotide recombinant from an appropriate template (Jellinek et al., supra, 1995).

The various components of the present invention comprise complexes of two or more oligonucleotides. The term "component" is used generally herein to denote a metastable structure of at least one propagating oligonucleotide bound to at least one damping oligonucleotide, wherein the propagating oligonucleotide possesses a bulge domain. Such metastable amplifier nucleic acid molecules are metastable only until it slightly disturbed (e.g., by the hybridizing of a target nucleic acid molecule or propagating oligonucleotide to a toehold domain of a damping oligonucleotide), wherein branch migration of the hybridizing molecule displaces the propagating oligonucleotide(s) from the damping oligonucleotide.

The term "propagating oligonucleotide" is used herein to denote one element of component of the invention (e.g., an amplifier nucleic acid molecule or a translator). The propagating oligonucleotide comprises a plurality of domains including at least two binding domains to the damping oligonucleotide, and at least one non-binding bulge region consisting of more than one domain. As disclosed herein, the amount of displaced propagating oligonucleotides increases exponentially over a period of time upon triggering (initiation) of an amplification system of the invention.

The term "damping oligonucleotide" is used herein to denote a second element of a component of the invention. The damping oligonucleotide comprises a plurality of domains, including at least one toehold domain and at least two propagating oligonucleotide binding domains. An excess of damping oligonucleotides can damp an amplification reaction because they selectively hybridize to complementary displaced propagating oligonucleotides.

As used herein, the term "amplifier nucleic acid molecule" or "amplifier" refers to a complex of a damping oligonucleotide and at least one propagating oligonucleotide, wherein, upon hybridization of the propagating oligonucleotide to the damping oligonucleotide, a bulge (loop) is present in the propagating oligonucleotide. Amplifier nucleic acid molecules are exemplified in FIG. 3, which shows a 3 component amplification system containing three gain2 amplifier nucleic acid molecules. As used herein, the term "gain" refers to the maximum number of propagating oligonucleotides selectively hybridized to a damping oligonucleotide in an amplifier nucleic acid molecule. For example, a "gain1" amplifier contains one propagating oligonucleotide bound to a damping oligonucleotide; a "gain2" amplifier contains two propagating oligonucleotides bound to a one damping oligonucleotide, etc.

Figure 3:
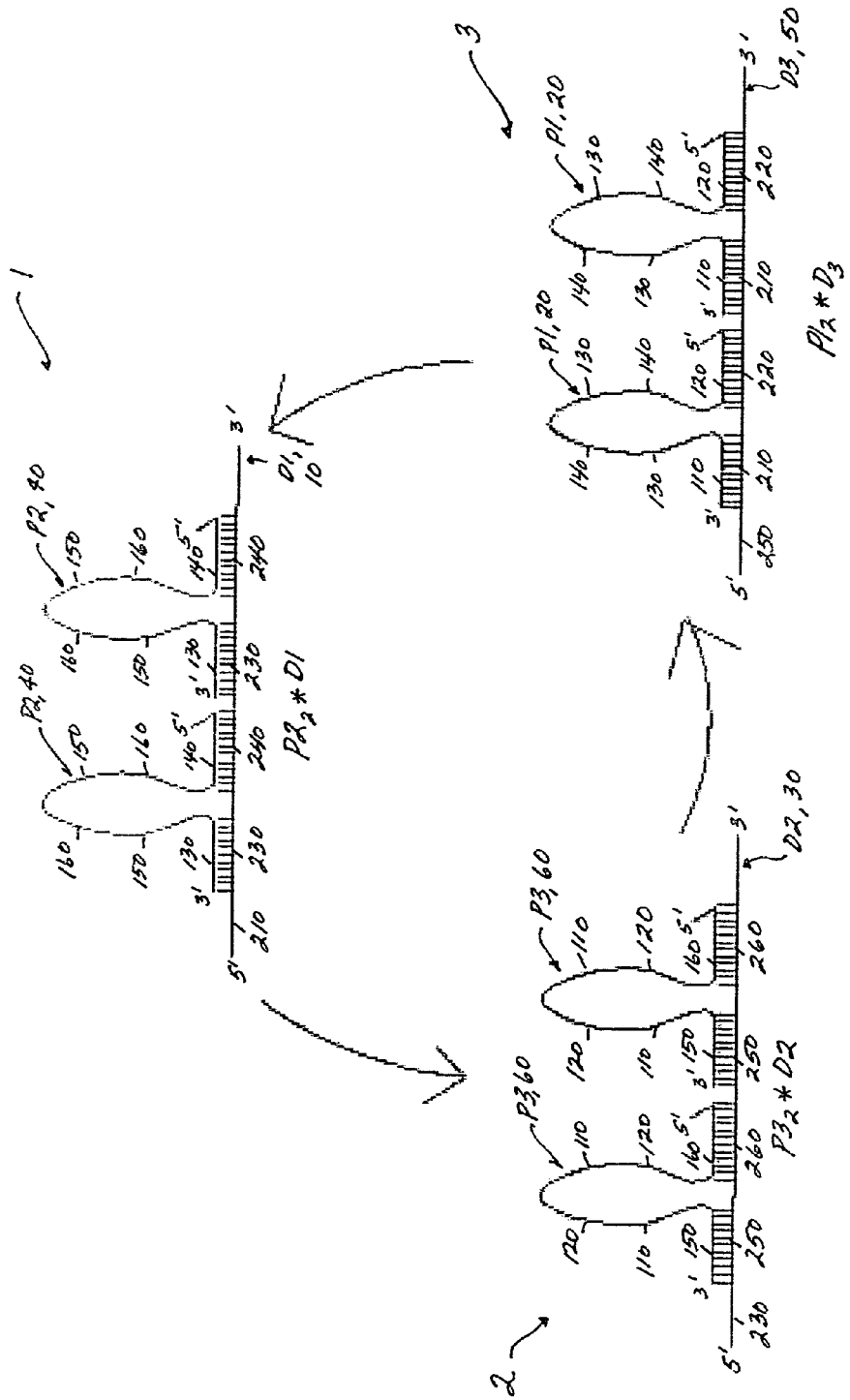
FIG. 3 illustrates a three component nucleic acid amplification system, including three gain2 components—amplifier nucleic acid molecule 1 ($P2_2$*D1), amplifier nucleic acid molecule 2 ($P3_2$*D2), and amplifier nucleic acid molecule 3 ($P1_2$*D3).

The term "nucleic acid amplification system" or "amplification system" refers to a combination of at least two amplifier nucleic acid molecules, wherein a propagating oligonucleotide of one amplifier is complementary to a damping oligonucleotide of a second amplifier, and wherein, for each damping oligonucleotide of the amplifiers, there is a complementary propagating oligonucleotide in one of the other amplifiers of the system. A three component (3 cycle) amplification system is shown in FIG. 3. As will be apparent, the amplifier nucleic acid molecules in an amplification system are related in that for each damping oligonucleotide (e.g., D1) of one amplifier, there is a propagating oligonucleotide (P1) in another amplifier that is sufficiently complementary to D1 such that, in an amplifier comprising D1, the P1 can hybridize by branch migration and displace one or more propagating oligonucleotides of the amplifier comprising D1.

Figure 5:
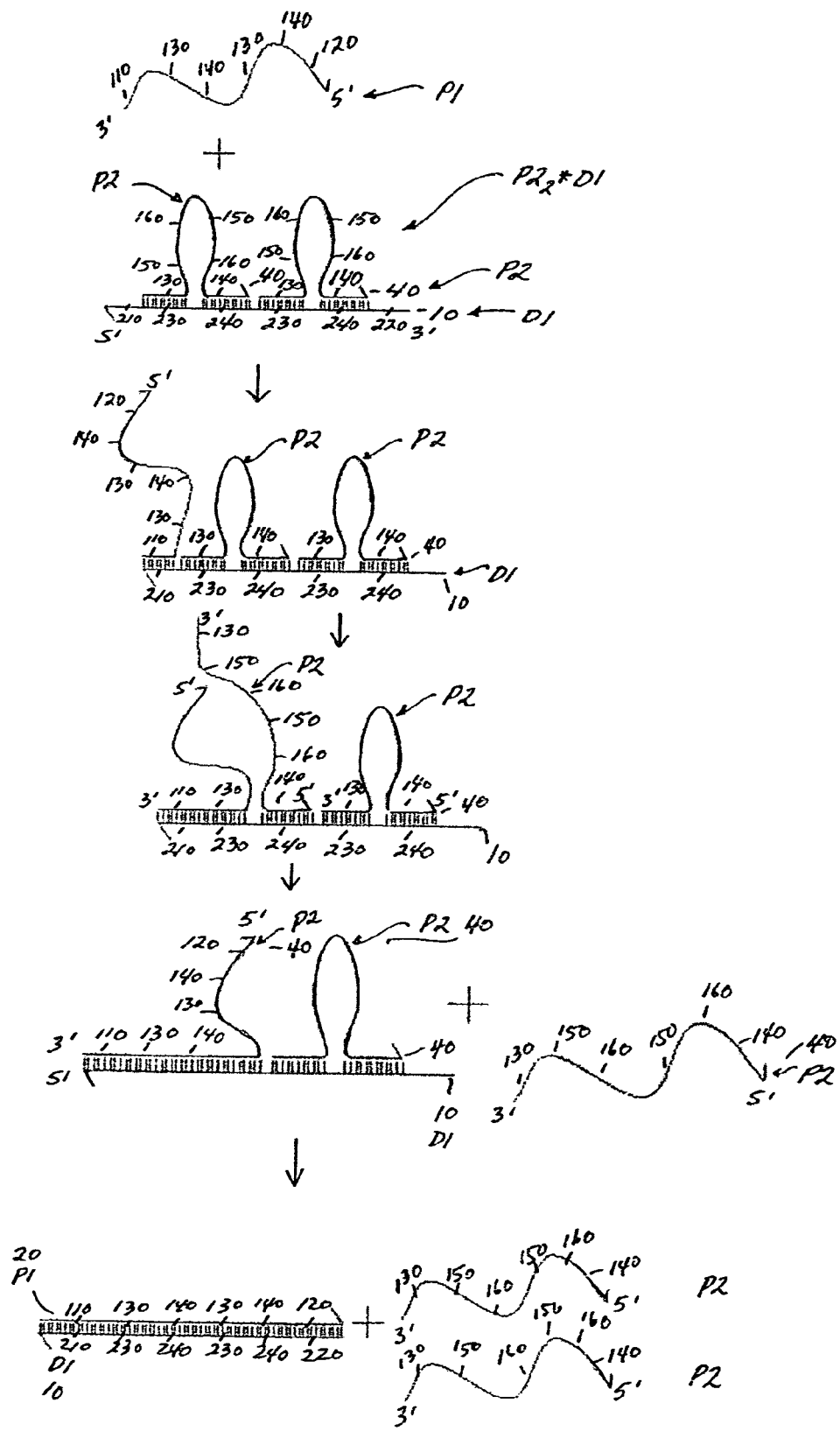
FIG. 5 shows an exemplary reaction involving an initiating oligonucleotide (P1) and one amplifier nucleic acid molecule 1 containing two propagating oligonucleotides (P2), and one damping oligonucleotide (D1). The reaction can be represented as—Reaction (1): $P1+P2_2$*$D1 \rightarrow P1$*$D1+2P2$.

FIG. 5 shows a reaction of free propagating oligonucleotide (P1) and a gain2 amplifier nucleic acid molecule (P2₂*D1). Free propagating oligonucleotide (e.g., P1) can selectively hybridize via 3' domain 110 to toehold domain 210 of damping oligonucleotide 10 (D1). Branch migration of P1 along D1 results in sequential displacement of the two propagating strands 40 (P2) from the amplifier. As such, a gain of 2 is obtained, wherein one propagating oligonucleotide (P1) displaces two propagating oligonucleotides (P2). A result of the reaction is that a P1*D1 hybrid is formed, which terminates the reaction with respect to these P1 and D1 molecules.

A translator nucleic acid molecule is used to convert a target nucleic acid molecule to an oligonucleotide that can initiate an amplification system of the invention. The term "translator" is used herein to denotes a combination of two gain1 components, one gain1 component of which can selectively hybridize to a target nucleic acid molecule, and the other of which contains a propagating oligonucleotide that can selectively hybridize to and branch migrate along a damping oligonucleotide of an amplifier nucleic acid molecule. A translator is exemplified in FIG. 2, wherein target sequence 100 can selectively hybridize via 3' domain 16 to toehold domain 26 of translator gain1 component 4 and, by branch migration displace propagating oligonucleotide 80, which can hybridize via domain 180 to toehold domain 280 of gain1 component 5 and, by branch migration, displace initiator propagating oligonucleotide 20 (P1). It will be recognized, in the present example, that P1 can selectively bind to and branch migrate along damping oligonucleotide 10 (D1) as shown in FIG. 3, thereby initiating amplification of an amplification system (see, also, FIG. 1). Notably, the translator converts a target nucleic acid molecule stoichiometrically in a 1:1 ratio into an initiator propagating oligonucleotide.

The oligonucleotides useful in the compositions of the invention comprise a number of operatively linked domains, including, for example, toehold domains operatively linked to propagating oligonucleotide binding domains in a damping oligonucleotide; and a damping oligonucleotide operatively associated with one or more propagating oligonucleotides in an amplifier. As used herein, the term "operatively linked" or "operatively associated" means that two or more molecules are positioned with respect to each other such that they act as a single unit and affect a function attributable to one or both molecules or a combination thereof. For example, a set of propagating oligonucleotide binding domains 230 and 240 are positioned in damping oligonucleotide 10 (D1; see FIG. 3) such that propagating oligonucleotide 40 (P2) can selectively hybridize via domains 130 and 140 such that a bulge is present in P2. Similarly, in an amplifier nucleic acid molecule, a propagating oligonucleotide is operatively associated with a damping oligonucleotide via selective hybridization of the flanking domains (e.g., domains 130 and 140 of P2) to the propagating oligonucleotide binding domains of the damping strand (e.g., domains 230 and 240 of D1).

The term "domain" is used herein to refer to a nucleotide sequence of an oligonucleotide that serves a particular function. For example, a toehold domain provides a nucleotide sequence that is complementary to a sequence of a second oligonucleotide such that the second oligonucleotide can selectively bind to the oligonucleotide containing the toehold domain. It should be recognized that, unless explicitly indicated otherwise, the terms "first", "second", "third", etc. are used only for convenience to distinguish different domains, oligonucleotides, and components. The terms are not meant to confer any importance, order, orientation or other feature or characteristic of a molecule.

The present invention provides compositions and methods that allow for detection of a target nucleic acid molecule and amplification of a signal that is indicative of the presence of the target nucleic acid molecule. As disclosed herein, the compositions can be combined to produce an amplification system that functions under isothermal conditions and without any requirement of enzymes such as polymerases. An amplification system useful for detecting and/or quantitating a target molecule includes at least two amplifier nucleic acid molecules, generally, but not necessarily, gain2 amplifiers or greater (e.g., gain3), which can be provided separately or in combination. In addition, the amplification system can include a translator system, which can be provided separately or in combination with one or more of the amplifiers. Upon contact of the translator system with a sample containing a target nucleic acid molecule, an amplification reaction is initiated.

The target nucleic acid molecule (target sequence) can be any nucleic acid molecule that can selectively hybridize to a toehold domain of a damping oligonucleotide, particularly a damping oligonucleotide of a component of a translator. The target sequence can be a gene sequence or portion thereof (e.g., a transcriptional and/or translational regulatory sequence, coding sequence, or intron-exon junction), a cDNA molecule, an RNA (e.g., an mRNA, tRNA or rRNA), or any other nucleic acid molecule, which can be an isolated nucleic acid molecule or a nucleic acid molecule contained in a sample (e.g., a cell sample, wherein the target nucleic acid molecule is an endogenously expressed molecule or is an exogenously introduced nucleic acid molecule or expressed from an exogenously introduce molecule), and can be a naturally occurring nucleic acid molecule or a synthetic molecule. A target sequence can be any length, provided that selective hybridization with a toehold domain can occur. A target sequence also can be contained within a larger nucleic acid molecule (e.g., a restriction fragment of genomic DNA).

The present compositions allow for the detection of a target nucleic acid molecule, when present, in a sample. The sample can be any sample that can contain a nucleic acid molecule, including, for example, a biological sample, environmental sample, or chemical sample. For example, a biological sample can be a cell, tissue, or organ sample, e.g., a cell sample of an established cell line, or a tissue sample obtained from a subject (e.g., via a biopsy procedure), or a biological fluid sample, and can be a sample of eukaryote or prokaryote, including a eukaryotic cell sample that is being examined, for example, for a target sequence of an infecting microorganism. An environmental sample that can be examined for the presence (or amount) of a target nucleic acid molecule can be, for example, a forensic sample (e.g., a blood sample or hair sample from a crime scene), a water or soil sample (e.g., to identify the presence of a contaminating organism), or a washing of a solid surface (e.g., a hospital surface to be examined for the presence of an infectious organism such as an antibiotic resistant bacterium).

The compositions and methods of the invention utilize selective hybridization to construct components and practice the methods. Selective hybridization includes the specific interaction of a sequence of a first polynucleotide with a complementary sequence of a second polynucleotide (or a different region of the first polynucleotide). As disclosed herein, selective hybridization of a damping oligonucleotide and a propagating oligonucleotide can generate amplifier nucleic acid molecules and translators, including complexes of two oligonucleotides, three oligonucleotides, four oligonucleotides, or more. As used here, the term "selective hybridization" or "selectively hybridize" refers to an interaction of two nucleic acid molecules that occurs and is stable under moderately to highly stringent conditions. The conditions required to achieve a particular level of stringency are well known and routine, and will vary depending on the nature of the nucleic acids being hybridized, including, for example, the length, degree of complementarity, nucleotide sequence composition (for example, relative GC:AT content), and nucleic acid type, i.e., whether the oligonucleotide or the target nucleic acid sequence is DNA or RNA.

Methods for selecting appropriate stringency conditions can be determined empirically or estimated using various formulas, and are well known in the art (see, for example, Sambrook et al., "Molecular Cloning: A laboratory manual" 2d Ed. (Cold Spring Harbor Laboratory Press 1989)). An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed. Hybridization conditions can be varied, for example, by including (or excluding) a reagent such as formamide from the reaction, and by correspondingly varying the salt and/or temperature of the reaction. As such, it will be recognized that various different reaction conditions can provide, e.g., highly stringent hybridization conditions.

For nucleic acid hybridization reactions, the conditions used to achieve a particular level of stringency will vary, depending on the nature of the nucleic acids being hybridized (see, e.g., Sambrook et al., supra, 1989; Short Protocols in Molecular Biology, ed. Ausubel, et al). Stringent conditions are sequence-dependent and will be different in different circumstances. For example, whether the oligonucleotide or the target nucleic acid molecule is DNA or RNA, can be considered in selecting hybridization conditions. Extensive guide to the hybridization of nucleic acids are described by Tijssen (Techniques in Biochemistry and Molecular Biology-Hybridization with Nucleic Acid Probes, "Overview of principles of hybridization and the strategy of nucleic acid assays", 1993). The hybridization conditions may also vary when a non-ionic backbone, i.e. peptide nucleic acids (PNAs) is used. A peptide nucleic acid backbone is made from repeating N-(2-aminoethyl)-glycine units linked by peptide bonds and do not contain pentose sugar moieties or phosphate groups; hence the backbone is not charged.

The generation of components and the practice of the methods of the invention can be accomplished in a variety of ways. For example, a reaction, including contact of a target sequence, a translator and/or amplifier nucleic acid molecule, can be performed by adding the various reagents together simultaneously, or sequentially, in any order. The reactions can include additional reagents, including, for example, salts, buffers, neutral proteins (e.g. albumin), and/or detergents, which can facilitate optimal hybridization and/or detection, and/or reduce non-specific or background interactions. Also, reagents that otherwise improve the efficiency of the detection assay and amplification reactions, such as protease inhibitors, nuclease inhibitors, anti-microbial agents, etc., can be included, depending, for example, on the sample preparation methods and purity of the target nucleic acid molecule. It should be recognized that, in control experiments, one or more of a target sequence, translator component, and/or amplifier may be omitted.

According to the present methods, a target sequence is identified by detecting the displacement of propagating oligonucleotides from amplifiers. The detection of such displacement can be facilitated by incorporating one or more detectable label in one or more of the amplifiers or an oligonucleotide comprising the amplifiers. The detectable label can be any molecule that conveniently can be linked to the oligonucleotide and detected using readily available equipment. For example, the detectable label can be a fluorescent compound such as TET, TAMRA, Cy3, Cy5, Fam, fluorescein, rhodamine (see, e.g., Synthegen; Houston Tex.), or a green fluorescent protein or enhanced or modified form thereof; a radionuclide such as sulfur-35, technicium-99, phosphorus-32, tritium or iodine-125; a paramagnetic spin label such as carbon-13, Gd-157, Mn-55, Dy-162, Cr-52, or Fe-56; a luminescent compound such as an aequorin; a chemiluminescent compound; a metal chelate; an enzyme such as luciferase or β-galactosidase, or a substrate for an enzyme; or a receptor or a ligand for a receptor, for example, biotin. Methods for linking a label to an oligonucleotide are well known in the art (see, for example, Hermanson, "Bioconjugate Techniques" (Academic Press 1996), which is incorporated herein by reference), as are method for detecting a particular label, such methods being selected based on the characteristics of the label.

Fluorescence resonance energy transfer (FRET) can provide a particularly convenient label for detecting dissociation of amplifier nucleic acid molecules, including displacement of a propagating oligonucleotide. FRET can be performed using a FRET pair, wherein a change in the secondary structure of a component comprising the FRET pair is indicated by a change in fluorescence. A FRET pair includes a fluorescent donor molecule and a fluorescent acceptor molecule. For FRET to occur, the fluorescence emission spectrum of the donor and that of the acceptor must overlap, and the donor and acceptor must be in close proximity. The distance between donor and acceptor at which 50% of donors are deactivated (i.e., do not emit photons due to transfer energy to the acceptor) is defined by the Forster radius, which typically is about 10-100 angstroms. Changes in the fluorescence emission spectrum of FRET pairs can be detected, and are indicative of changes in the number of donors and acceptors that are in close proximity. Compositions and methods for using FRET are routine and well known (see, e.g., U.S. Pat. No. 6,737,244, which is incorporated herein by reference).

FRET is a distance-dependent interaction between the electronic excited states of two dye molecules. Thus, FRET can be used to study structure and conformation of nucleic acids and detection of nucleic acid hybridization as in the present invention. Furey et al., *Biochemistry* 37, 2979-2990 (1998); Parkhurst et al., *Biochemistry* 34, 285-292 (1995). FRET can utilize a first fluorescent molecule and a second fluorescent molecule, or can utilize a fluorescent molecule and a quencher, which quenches the fluorescence of the fluorescent molecule. Fluorescent moieties useful as fluorescent labels or as a fluorescent acceptor or donor of a FRET pair are well known and include, for example, fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo)benzoic acid (DABCYL), and 5-(2'-aminoethyl)aminonaphthalene-1-sulfonic acid (EDANS). Other potential FRET donor or acceptor molecules are known in the art (see, e.g., U.S. Pat. Nos. 5,866,336 and 6,737,244, each of which is incorporated herein by reference).

Typically, the donor and acceptor dyes are different, in which case FRET can be detected by the appearance of sensitized fluorescence of the acceptor or by quenching of donor fluorescence. However, when the donor and acceptor are the same, FRET can be detected by the resulting fluorescence depolarization. Examples of FRET donor/acceptor pairs include fluorescein/tetramethylrhodamine; IAEDANS/fluorescein; EDANS/Dabcyl; Fluorescein/Fluorescein; BODIPY FL/BODIPY FL; and Fluorescein/QSY 7 and QSY 9 dyes. Probes incorporating fluorescent donor—nonfluorescent acceptor combinations have been developed primarily for detecting nucleic acid hybridization (Marras et al., *Nucleic Acids Res.* 30, e122, 2002).

The methods of the invention can be performed in any of various formats, including, for example, as a single assay to detect a target nucleic acid molecule in a sample; or in a multiplex format, wherein a plurality of target sequences are examined in a single sample. The use of FRET using differentially labeled amplifiers can be particularly useful for performing a multiplex analysis because spectrometry can readily detect different fluorescence energy signals. Further, the methods conveniently can be adapted to and performed in a high throughput format, wherein a plurality of samples, some or all of which can contain one or a plurality of target sequences, can be examined in parallel.

High throughput (or ultrahigh throughput) assays provide the advantage that numerous samples can be examined in parallel, thus allowing, for example, for the inclusion of appropriate controls, or for the examination of several different samples under substantially identical conditions, or for the examination of several same samples under different conditions. Further, high throughput assays are readily adaptable to automation, thus reducing costs, as well as reducing the potential for random errors. A high throughput assay can be performed, for example, in wells of a plate (e.g., 96 well, 384 well, or 1536 well plates), or in delineated regions (e.g., 10, 100, 1000, 10,000, or 100,000 delineated regions) of a chip or glass slide. For example, a solid support such as a silicon based chip or glass slide can be modified to contain pits, into which a sample can be deposited. In one embodiment, the samples are deposited in a defined pattern such as array, which can be an addressable array. An addressable array can facilitate identification of particular samples, as well as automation of the types, times, and amounts of one or more reagents, and the like added to and/or removed from the sample, and examination of the amplification signal, if any, produced according to the methods.

The present invention also relates to a kit, which contains components useful for identifying a target nucleic acid molecule. A kit of the invention can contain, separately or as a mixture, two or more amplifier nucleic acid molecules that can generate an amplification signal (e.g., a 2 cycle amplification system, or a 3 cycle amplification system), and one or a plurality of translators (e.g., different translators specific for different target sequences). A kit of the invention also can contain one or more other component(s) that can be useful for practicing the present methods and/or analyzing the results. For example, the kit can contain a component that can be useful as a control, or for standardizing an assay, (e.g., a known target nucleic acid molecule, which can be in a defined amount).

By way of example, an amplification system can include three gain2 components. For convenience, the propagating oligonucleotides are named P1, P2, and P3, and the complementary damping oligonucleotides are named D1, D2, and D3. Further, the three gain2 components are denoted as $P2_2{*}D1$ 1, $P3_2{*}D2$ 2, and $P1_2{*}D3$ 3 (see, also, FIG. 3). Additional amplification systems are exemplified by two gain2 components, three gain2 components, four gain2 components, five gain2 components, etc. The components (e.g., $P2_2{*}D1$ 1, $P3_2{*}D2$ 2, and $P1_2{*}D3$ 3) can be preformed by annealing, preferably such that few or no free species of propagating oligonucleotides (P1, P2, and/or P3) remain. The amplifiers are metastable as long as there are no free propagating oligonucleotides that can trigger (or initiate) amplification.

Each oligonucleotide consists of a plurality of domains. The toehold domain, for example, serves to increase the rate of kinetics by binding to a complementary domain on another oligonucleotide. Toehold domains reside on damping oligonucleotides, or any oligonucleotide which hybridizes to complementary domains on a target nucleic acid molecule and/or initiating or propagating oligonucleotides. The hybridization of propagating oligonucleotide(s) to a damping oligonucleotide, and a damping oligonucleotide to a target sequence colocalizes the oligonucleotides such that a complex forms. Toehold domains can be of varied length, and generally are at least two nucleotides in length (e.g., 2, 3, 4, 5, 6, 7, 8, 9, 10, or more), and can be forty nucleotides in length or greater. In addition, a toehold domain can be positioned 5' to the propagating oligonucleotide binding domains of a damping oligonucleotide, as generally exemplified herein, or can be positioned 3' to the propagating oligonucleotide binding domains.

A toehold domain of at least two nucleotides in length of a first oligonucleotide (e.g., a damping oligonucleotide) is sufficient for selective hybridization to a second oligonucleotide (e.g., a propagating oligonucleotide) having a complementary nucleotide sequence. While such a two nucleotide region of complementary generally is not stable for long periods of time, the hybridization is sufficient such that branch migration can proceed, thereby stabilizing the interaction of the first and second oligonucleotides. Such hybridization of two nucleotide overhangs is known to occur, for example, with respect to overhangs due to restriction endonuclease cleavage, wherein the hybridized ends can be stabilized by ligation with a ligase. In addition, selective hybridization of 2 nucleotide 3' overhangs of siRNA occurs (see, e.g., Ma et al., *Nature*, 429(6989):318-22 (2004); stating that "In a sequence-independent manner, PAZ {the PAZ domain is an RNA-binding module found in Argonaute and some Dicer proteins} anchors the 2-nucleotide 3' overhang of the siRNA-like duplex within a highly conserved binding pocket, and secures the duplex by binding the 7-nucleotide phosphodiester backbone of the overhang-containing strand and capping the 5'-terminal residue of the complementary strand.").

An advantage of the present invention is that colocalization of oligonucleotides (e.g., a propagating oligonucleotide of a first amplifier and a damping oligonucleotide of a second amplifier) is accomplished under isothermal conditions. As such, an amplification reaction can be performed in the absence of thermo-cycling. Thermo-cycling is not required for amplification because the nucleic acid secondary structures of the compositions of the invention drive the reactions.

The amplification system is typically prepared just prior to the actual use by mixing the three pre-annealed gain2 components (e.g., $P2_2{*}D1$ 1, $P3_2{*}D2$ 2, and $P1_2{*}D3$ 3). Upon mixing of the amplifiers, the target nucleic acid molecule and translator can be added, and the reaction can be followed over a period of time (observation window) to detect the generation of a signal. As used herein, the term "observation window" denotes the length of time from the time after a sample comprising a target nucleic acid molecule is contacted with an amplification system such that amplification is initiated. The observation window can be varied, as desired, from a few seconds (e.g., 10, 20, 30, etc. seconds), to a few minutes (1, 2, 3, 4, 5, 10, 20, 30, etc. minutes), to a few hours (e.g., 1, 2, 3, 4, 5, 6, 7, 8, 10, 12, 15, 20, 24, 48, or more hours).

Figure 4:
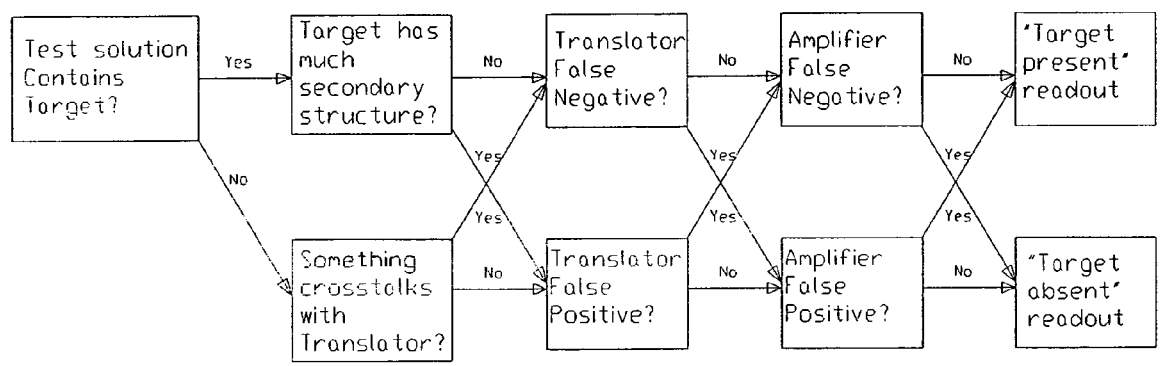
FIG. 4 shows a flowchart of the logic used to detect the presence of a target nucleic acid molecule.

FIG. 4 provides an indication as to errors that can occur at various stages of an amplification reaction. For example, a false positive result can occur at the translator phase (conversion of target nucleic acid into a propagating oligonucleotide) if a target nucleic acid molecule has increased secondary structure. Additional sources of error, and methods of correcting for them are disclosed below.

The following examples illustrate the present invention.

EXAMPLE 1

Preparation of a Translator for Conversion of a Target Sequence to a Propagating Oligonucleotide A translator is composed of two gain1 components (one propagating oligonucleotide to one damping oligonucleotide for each component; 1:1 ratio). The nucleotide and domain sequences of the translator gain1 components are fixed, relative to the desired target sequence and the gain2 components in the amplification system. Hence, the two gain1 components of the translator are modified as the target sequence changes (see FIG. 2). As such, there is a unique translator for every target sequence. The target sequence and its converted propagating oligonucleotide, which is dependent on at least one propagating oligonucleotide (P1, P2 or P3) of the amplification system, determine the sequence design of every oligonucleotide (70, 80, 90 and 20) used in the translator system (see FIG. 2).

Figure 2:
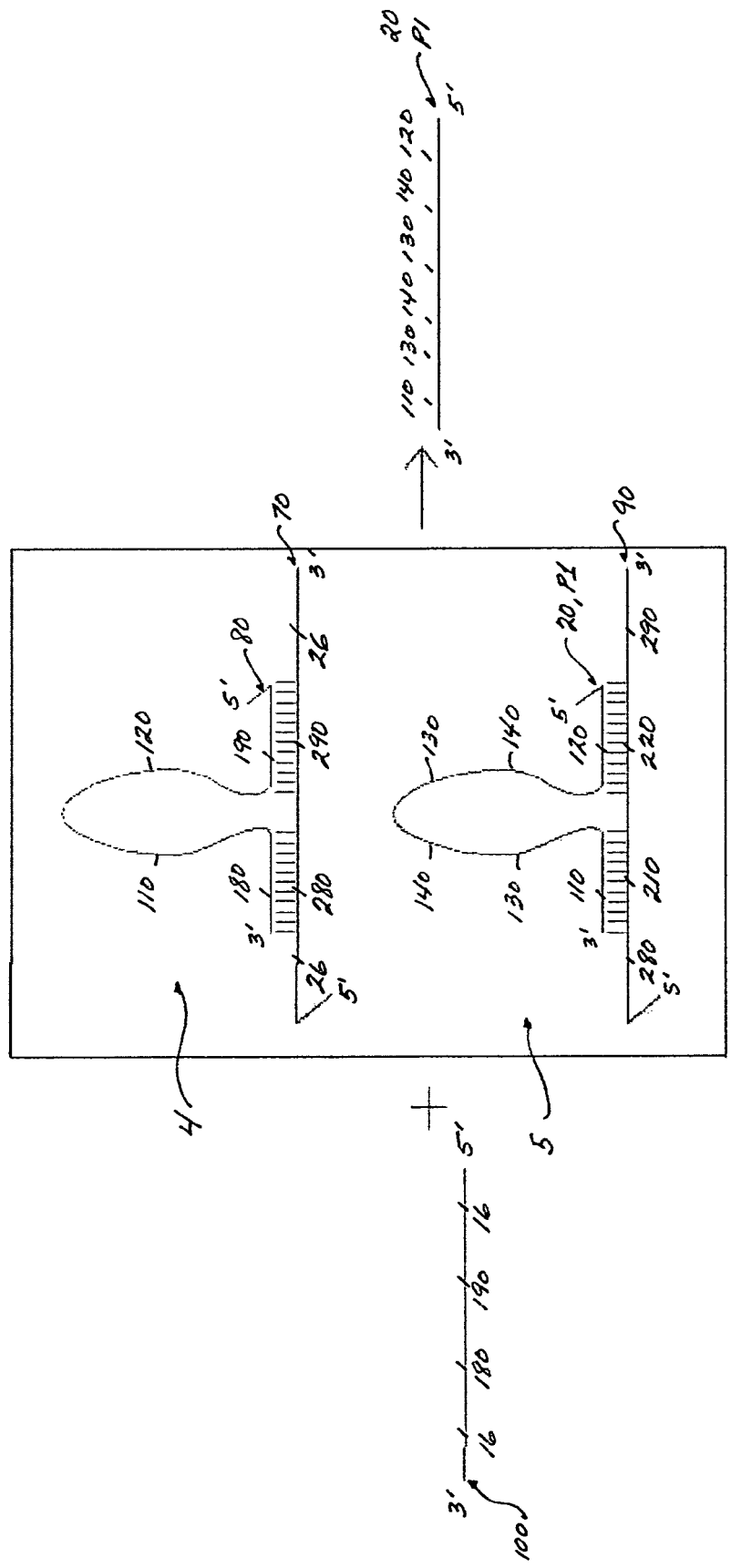
FIG. 2 illustrates a two gain1 translator system, including first gain1 translator 4 and second gain1 translator 5. Target nucleic acid molecule 100 and initiator propagating oligonucleotide 20 also are shown.

The oligonucleotide that triggers the amplification system is one of the three propagating oligonucleotides (P1, P2 or P3) of an amplifier (e.g., the P1 oligonucleotide; see FIG. 2). There is a fixed set of oligonucleotides across all reactions for the amplifier (e.g., P1, P2, and P3, and D1, D2 and D3). This uniformity or consistency is reconciled with the fact that the target sequence can be converted to an arbitrary sequence with the use of the translator; an arbitrary sequence can be designed to be identical to that of one of the propagating oligonucleotides in the amplification system.

The target sequence can be any nucleic acid molecule of interest. Referring to FIG. 2, the first damping oligonucleotide 70 of the first gain1 component 4 contains at least one toehold domain 250 that can selectively hybridize to a complementary domain of the target sequence. The second damping oligonucleotide 90 of the second gain1 component 5 contains at least one toehold domain 280 that can selectively hybridize to the complementary domain of the first propagating oligonucleotide 80.

EXAMPLE 2

Conversion of a Target Sequence to a Propagating Oligonucleotide in a Stoichiometric Ratio 1:1

The presence of the target sequence in solution is detectable only if the target sequence is first converted to a propagating oligonucleotide which is capable of initiating an amplification system or feedback loop mechanism (see FIG. 2). FIG. 2 shows a translator composed of two gain1 components 4 and 5. The first gain1 component 4 consists of a damping oligonucleotide 70 and a bound propagating oligonucleotide 80. The two oligonucleotides 70 and 80 are selectively hybridized together at sequence domains 180 and 190, in the 3' to 5' direction, of the propagating oligonucleotide 80, and 280 and 290, in the 5' to 3' direction, of the damping oligonucleotide 70. The damping oligonucleotide 70 contains at least one more binding domain 26, a toehold binding domain for the target sequence 8. The second gain1 component 5 also consists of a damping oligonucleotide 90 and a propagating oligonucleotide 20 (or P1). The propagating oligonucleotide 20 and the damping oligonucleotide 90 are selectively hybridized together at sequence domains 110 and 120, in the 3' to 5' direction, of the propagating oligonucleotide 20, and 210 and 220, in the 5' to 3' direction, of the damping oligonucleotide 90. The damping oligonucleotide 90 contains at least one more domain, or at least two more domains, at the 5' and 3' ends, for example, sequence domain 280 and 290.

The damping oligonucleotide 70 is complementary to the target sequence. For example, in FIG. 2, the target sequence 8 is 16-180-190-16, in the 3' to 5' direction, and the damping oligonucleotide 70 sequence is 26-280-290-26, in the 5' to 3' direction. The domain 16 of the target sequence 8 binds to the toehold domain 26 of the damping oligonucleotide 70. Branch migration of the target sequence 8 to the damping oligonucleotide 70 displaces the propagating oligonucleotide 80. The target sequence forms an inert two oligonucleotide complex with the damping oligonucleotide 70.

The displaced propagating oligonucleotide 80 then binds to the toehold domain 280 of the damping oligonucleotide 90. Branch migration of the propagating oligonucleotide 80 to the damping oligonucleotide 90 displaces the propagating oligonucleotide 20. The propagating oligonucleotide 80 forms an inert two oligonucleotide complex with the damping oligonucleotide 90.

The conversion of the target sequence 8 to a propagating oligonucleotide 20 is at a 1:1 ratio, one target sequence for every one propagating oligonucleotide 20. The displaced propagating oligonucleotide 20 is ready to initiate amplification of other propagating oligonucleotides of the amplification system.

EXAMPLE 3

Binding of Propagating Oligonucleotide to a Damping Oligonucleotide Triggers Amplification The converted target sequence (i.e., the initiator propagating oligonucleotide 20) can trigger an amplification system, as exemplified in FIG. 3 by a three gain2 component amplification system. The first cycle proceeds via the gain2 component 1, as illustrated in FIG. 5; the second, and third cycles function in substantially the same way. The translator output (initiator propagating oligonucleotide sequence 20; P1) is identical to the propagating oligonucleotides 20 (P1) of the gain2 amplifier 3, and is substantially complementary to the damping oligonucleotide 10 of the gain2 amplifier 1.

The three cycles of the amplification system can also be described in reactions sets (1), (2) and (3) below. The first cycle is represented by reaction (1); the second cycle by reaction (2); and the third cycle by reaction (3). The basic reaction set includes:

$$P1 + P2_2{*}D1 \rightarrow P1{*}D1 + 2P2 \qquad (1)$$

$$P2 + P3_2{*}D2 \rightarrow P1{*}D1 + 2P3 \qquad (2)$$

$$P3 + P1_2{*}D3 \rightarrow P3{*}D3 + 2P1 \qquad (3)$$

In the first cycle, or reaction (1), a propagating oligonucleotide 20 (P1) selectively hybridizes to at least one gain2 component $P2_2{*}D1$, 1 via the toehold domain 210 of the damping oligonucleotide 10. Reaction (1) is shown in detail in FIG. 5. FIG. 5 shows a first propagating oligonucleotide 20

(P1; 3'-110-130-140-130-140-120-5') which is substantially complementary to a first damping oligonucleotide 10 (D1; 5'-210-230-240-230-240-220-3') of the gain2 component 1. In FIG. 5, the 3'-110 domain of P1 hybridizes to the 5' toehold domain, or the 5'-210 domain of D1. Branch migration of the propagating oligonucleotide (P1) along the damping oligonucleotide 10 (D1) sequentially displaces the first and second propagating oligonucleotides 40 (P2), which are bound to the damping oligonucleotide 10 (D1) at binding domains 130, 140, 130, and 140 (see FIG. 3). The hybridization of propagating oligonucleotide 20 (P1) with the substantially complementary damping oligonucleotide 10 (D1) forms an inert two oligonucleotide complex. The sequence of the displaced propagating oligonucleotides 40 (P2) is 3'-130-150-160-150-160-140-5'.

In the second cycle (reaction 2), each of the two propagating oligonucleotides 40 (P2) similarly displaces two propagating oligonucleotides 60 (P3) in reaction (2) by hybridizing to two second gain2 components $P3_2$ *D2 2 via the toehold domains 230 of the damping oligonucleotide 30. By branch migration, each of the two P2 sequentially displaces two P3 (2P3) of each second gain2 component 2 such that, at the end of the second cycle (reaction 2), four P3 propagating oligonucleotides 60 have been displaced.

In the third cycle (reaction 3), the kinetics are substantially similar as in the first cycle and second cycles. Each of the four propagating oligonucleotides 60 (P3) selectively hybridizes to two third amplifier gain2 components $P1_2$*D3 3 via the toehold domains 250, and by branch migration, each of the four propagating oligonucleotides 60 ($2P3_2$=4 P3) displaces each of the two propagating oligonucleotide 20 ($P1_2$), of each third gain2 component. As such, in the first cycle, two propagating oligonucleotides are displaced, in the second cycle, four propagating oligonucleotides are displaced, and in the third cycle eight propagating oligonucleotides are displaced. Therefore, reactions (1), (2) and (3) combine to make 14 propagating oligonucleotides (2P2, 4P3 and 8P1).

The amplification system having three gain2 components described above is only one example of a system of the invention; other amplification systems can have fewer or more gain2 components. For example, an amplification system can have two gain2 components (or loop size 2), or can have, e.g., one gain2 component and two gain1 components, and generally does not have only one gain2 (or loop size 1) because once the triggering propagating oligonucleotide hybridizes to the toehold domain of the damping oligonucleotide, a kinetically and energetically favorable two oligonucleotide complex forms, stopping the reaction. Although there are two propagating oligonucleotides displaced, the displaced propagating oligonucleotides cannot hybridize to a free toehold of any damping oligonucleotide. Thus, with the hybridization of a substantially complementary propagating and damping oligonucleotide pair, the amplification process terminates.

The gain number of an amplifier can be as high as desired. As will be evident, however, increasing gain number also means changing other aspects of the system, including increasing damping oligonucleotide length and adding more complementary binding domains, redesigning the translator gain1 components such that the output propagating oligonucleotide is identical to at least one propagating oligonucleotide of the higher gain amplification system, and complementary to at least one damping oligonucleotide of the higher gain amplification system as well.

EXAMPLE 4

Preparation of Gain1 and Gain2 Components

Each gain1 or gain2 component is prepared individually. For example, preparation of the gain2 component 3 ($P1_2$*D3) is shown in reaction (4), below, whereby two propagating oligonucleotides 10 (P1) and one damping oligonucleotide 40 (D3) are mixed in solution resulting in the metastable $P1_2$*D3 component 3. The other two gain2 components, $P3_2$*D2 2 and $P2_2$*D1 1 are described in reactions (5) and (6), and are formed in substantially the same manner as in reaction (4), mixing the respective propagating (P2 and P3) and damping oligonucleotides (D2 and D1).

$$2P1+D3 \rightarrow P1_2*D3 \qquad (4)$$

$$2P2+D1 \rightarrow P3_2*D2 \qquad (5)$$

$$2P3+D2 \rightarrow P2_2*D1 \qquad (6)$$

Each gain2 component ($P1_2$*D3 3, $P3_2$*D2 2 and $P2_2$*D1 1; reactions (4) to (6)) is prepared separately because, if all six or all eight oligonucleotides are mixed in their single-stranded state, then proper components may not form because complementary oligonucleotide complexes such as P1*D1, P2*D2 and P3*D3 are energetically and kinetically favored. Prior to annealing and forming the gain2 components proper oligonucleotide concentrations are determined such that a stoichiometric ratio of about 1.98:1 is obtained. Concentrations of about 0.10 nM to about 10 μM of each nucleotide are prepared, then the individual gain2 components are formed by mixing the proper ratio of the individual oligonucleotides (e.g., two propagating oligonucleotides to one damping oligonucleotide for a gain2 component). To properly anneal the individual oligonucleotides to form gain2 components, standard nucleic acid annealing is performed. For example, the individual oligonucleotide solution can be heated to a high temperature (e.g., about 95° C.) to remove all secondary structure of the oligonucleotides, then the solution is slowly cooled to about room temperature; slow cooling ensures that the thermodynamically most-favored secondary structures result. By keeping the design of the gain1 and gain2 component secondary structures relatively simple, annealing need not be performed too slowly. An example of temperatures used for annealing is provided in Table I.

TABLE I

One Exemplar of an Amplification Procedure

| Step | Temp. (° C.) | Time (s) |
|------|--------------|----------|
| 1 | 95 | 300 |
| 2 | 94.9 | 6 |
| 3 | 94.8 | 6 |
| ... | ... | 6 |
| 599 | 35.2 | 6 |
| 600 | 35.1 | 6 |
| 601 | 35.0 | 12 |
| 602 | 34.7 | 12 |
| 603 | 34.4 | 12 |
| ... | ... | 12 |
| 700 | 20.3 | 12 |
| 701 | 20 | HOLD |

To perform an amplification reaction, the amplifiers, target sequence and translator are combined, then mixed vigorously, for example, by shaking the test tube manually, by vortexing with an electronic vibration plate, by stirring with a stir bar, or by any standard mixing method as known in the art. Upon mixing all three gain2 components with the target and translator solutions, the presence of the target sequence is indicated by the exponential growth of propagator oligonucleotide signals, which if fluorescently labeled, for example, can be detected as a macroscopic change in fluorescent signal.

EXAMPLE 5

Reactions between Complete and Incomplete Gain2 Components

The six reactions (1-6) presented above are sufficient to describe the behavior of an amplification system. However, other reactions also can occur, and the effects can be minimized as discussed below.

Ideally, each gain2 component has a ratio of two propagating oligonucleotides to one damping oligonucleotide achieving (2:1). However, preparing gain2 component in a perfect 2:1 is difficult because any excess propagating oligonucleotide(s) can trigger the amplification system upon mixing of the three components. This effect can be minimized by using an excess of damping oligonucleotides in preparing an amplifier (e.g., a gain2 component). A slight excess of damping oligonucleotides (e.g., a ratio of propagating to damping oligonucleotides of about 1.98:1) can prevent unwanted triggering of the amplification system.

While a 1.98:1 stoichiometry of propagating to damping oligonucleotides prevents unwanted triggering of the amplification system, it also can result in formation of incomplete components, such as P1*D3 (one propagating oligonucleotide to one damping oligonucleotide, 1:1 ratio). The ratio of $P1_2$*D3 to P1*D3 to free D3 follows a quadratic distribution (i.e. $p^2:2pq:q^2$). The quadratic distribution is a consequence of the fact that, in the formation of components, the propagating oligonucleotides are attached sequentially to the damping oligonucleotide. That is, each gain2 component in reactions (4), (5) and (6) is a net reaction. For example, if propagating oligonucleotides (P1) and damping oligonucleotides (D3) are mixed in 1:1 ratio in solution, approximately ¼ of the solution are completely formed components ($P1_2$ *D3), ½ of the solution are incompletely formed components (P1*D3), and ¼ of the solution are free damping oligonucleotides (D3). The incomplete component, although similar to a gain1 component, contains additional propagating oligonucleotide binding domains on the damping oligonucleotide. As such, incomplete components, including P1*D3, P2*D1 and P3*D2, can compete with properly formed gain2 components (see, reactions (10), (11) and (12), below).

Upon the mixture of all three gain2 component solutions and triggering of the amplification system by an excess propagating oligonucleotide, other reactions occur due to the presence of free damping oligonucleotides and incomplete components. Reactions (7), (8) and (9) below represent the hybridization of propagating oligonucleotides to free damping oligonucleotides. For example, in reaction (7), a first propagating oligonucleotide (P1; 3'-110-130-140-130-140-120-5') binds to its substantially complementary damping oligonucleotide (D1; 5'-210-230-240-230-240-220-3'); in reaction (8), the second propagating oligonucleotide (P2; 3'-130-150-160-150-160-140-5') binds to its substantially complementary damping oligonucleotide (D2; 5'-230-250-260-250-260-240-3'); and in reaction (9), the third propagating oligonucleotide (P3; 3'-150-110-120-110-120-160-5') binds to its substantially complementary damping oligonucleotide (5'-250-210-220-210-220-260-3'; see Table II for oligonucleotide sequence domains. Thus, reactions (7), (8) and (9) produce complementary two oligonucleotide complexes that are energetically and kinetically favored.

P1+D1→P1*D1     (7)

P2+D2→P2*D2     (8)

P3+D3→P3*D3     (9)

The products of reactions (7), (8) and (9) can compete with complete and properly formed gain2 components from reactions (1), (2) and (3), and can contribute to false negatives, because the products (P1*D1, P2*D2 and P3*D3) of reactions (7), (8) and (9) are in their unreactive ground states. Further, incomplete components (P1*D3, P2*D1 and P3*D2) can react with excess propagating oligonucleotides in reactions (10), (11) and (12) below, and compete with complete gain2 components of reactions (1), (2) and (3). For example, in reaction (10), incomplete component P2*D1 reacting with excess propagating oligonucleotide (P1), can result in the inert and substantially complementary two oligonucleotide complex (P1*D1) and a free second propagating oligonucleotide (P2). Reactions (11) and (12) are similar in that the mixture of incomplete components with excess propagating oligonucleotides can generate inert and complementary two oligonucleotide complexes (P2*D2 and P3*D3). Thus, both incomplete components (P1*D3, P2*D1 and P3*D2) and complete components ($P1_2$*D3, $P2_2$*D1 and $P3_2$*D2) compete for excess propagating oligonucleotides (P1, P2 or P3).

P1+P2*D1→P1*D1+P2     (10)

P2+P3*D2→P2*D2+P3     (11)

P3+P1*D3→P3*D3+P1     (12)

Although, reactions (10), (11) and (12) do not contribute directly to false negatives, they can slow down the rate of exponentiation of the amplification.

EXAMPLE 6

Detection of Target Sequences Using Fluorescent Dye/Quencher Pairs

Detection of the presence of the target sequence is exemplified by use of fluorescent dye/quencher pairs. For example, a fluorescent dye can be attached to the 3' end of a propagating oligonucleotide and a corresponding quencher can be attached to the 5' end. A propagating oligonucleotide, in the native ("untriggered") state, has a secondary loop (or bulge) structure, such that the 3' end which is fluorescently labeled is close in proximity to the 5' end, which has the corresponding quencher. The close proximity of the dye to the quencher, quenches the signal of the dye. As such, in the absence of a target sequence, there is no amplification of propagating oligonucleotides, and the propagating oligonucleotides remain in their native state in an amplifier nucleic acid molecule. In contrast, upon selective hybridization and branch migration of a triggering propagating oligonucleotide to a damping oligonucleotide, displacement of the propagating oligonucleotides of the amplifier results in the 5' and 3' ends no longer being maintained in close proximity to each other, and the quencher no longer quenches the fluorescent signal. The separation of the fluorescent label and its quencher produces an increase in fluorescence, which can be visualized, for example, using a spectrophotometer (in case of dilute solutions or minimal amplification), or by the naked eye (in case of concentrated solutions or high levels of amplification). The present compositions and methods can provide exponential amplification of a single molecule to $10^{15}$ molecules in a reasonable observation time.

EXAMPLE 7

Effect of Salt and Other Solutes on Amplification Kinetics

Various solutes and buffers facilitate hybridization of various oligonucleotides. The oligonucleotides are charged molecules and, therefore, a salt buffer is useful to ease the structure of the negatively-charged nucleic acid backbone and facilitate hybridization (e.g., TAE containing 12 mM $Mg^{2+}$). However, while increased salt concentration tends to make nucleic acid hybridization more energetic, the increased salt can affect the kinetics of the amplification system. For example, in reaction (1) (see FIG. 5), the rate of the first step of hybridization of the propagating oligonucleotide 20 (P1) to the damping oligonucleotide 10 (D1) via the toehold domain 210 is increased with higher salt concentrations. Conversely, the energetic binding of the propagating oligonucleotide 20 (P1) and the damping oligonucleotide 10 (D1) means that the branch migration process and subsequent and sequential displacement of the two propagating oligonucleotides 40 ($P2_2$) is slow. Further, depending on other conditions, either the toehold binding or the branch migration can be the rate-limiting step of this reaction (1), and is affected by varying salt concentrations.

EXAMPLE 8

Effect of Component Concentration on Amplification Kinetics

Gain1 and/or gain2 component concentrations can be varied. For example, at higher concentrations, two oligonucleotide and three oligonucleotide complexes, or more, are likely although as the concentration of oligonucleotides increases, dimers, trimers, etc. of the amplifier molecules can form. If desired, such dimer, trimer, etc. formation can be minimized by examining the complex formation, for example, using a gel electrophoretic mobility assay, and the concentration of oligonucleotides can be adjusted accordingly. On the other hand, at lower gain1 and/or gain2 component concentrations, the kinetics of the exponential amplification is slower. Additionally, for the purposes of detection, if fluorescent dye-labels are used, the fluorescent signal is weaker at lower gain1 and/or gain2 component concentrations. Preliminary tests were performed using concentrations from about 10 nM to about 100 nM of each gain1 and/or gain2 component (i.e. total concentration of 200 nM of each propagating oligonucleotide and 100 nM of each damping oligonucleotide). The dissociation rate of propagating oligonucleotides for an amplifier nucleic acid molecule containing a five nucleotide first toehold domain at 20° C. was $1.3*10^4$.

EXAMPLE 9

Error-Reduction Modifications

Certain errors can occur throughout the detection and amplification steps, including false negatives and false positives. A false negative can occur, for example, when the reaction (target sequence+translator+amplification system) contains the target sequence, but exponential amplification does not occur. A false positive can occur, for example, when the reaction (target sequence+translator+amplification system) does not contain the target sequence, but exponential amplification proceeds.

High false negative rates tend to decrease the sensitivity of detection. If, in each instance, the target sequence has a 20% probability of triggering the exponential amplification (i.e. 80% false negative per oligonucleotide), then the sensitivity threshold is 5 molecules. Amplification is expected in the presence of more than 5 molecules of the target sequence in the solution (target sequence+translator+amplification system). If the false negative rate per oligonucleotide is 99.99%, then the sensitivity threshold is 10,000 molecules, which is in the range of what is considered acceptable. Thus, there is a degree of flexibility concerning false negatives in the detector.

There are several sources of false negative results. First, to prevent high false positive rates, the stoichiometric ratio of the component parts is less than about 2:1 ratio of propagating to damping oligonucleotides (i.e. 1.98:1). This ratio implies the existence of some free damping oligonucleotides, as well as incomplete 1:1 components as discussed above. As such, if a propagating oligonucleotide hybridizes to a free damping oligonucleotide, which has no other propagating oligonucleotide attached, and if the propagating oligonucleotide is labeled with a dye-quencher pair, the dye-signal is lost. However, if the propagating oligonucleotide hybridizes with an incomplete 1:1 component, there is one output propagating oligonucleotide generated for each input propagating oligonucleotide consumed; see reactions (10), (11) and (12). In reactions (10), (11) and (12), if the propagating oligonucleotides are labeled, there is no amplification of dye-signal, and the output propagating oligonucleotide participates in another reaction by binding to a free version of its substantially complementary damping oligonucleotide.

Second, if the target sequence possesses high secondary structure, the target sequence may not be converted into a propagating oligonucleotide that triggers the amplification system due to kinetic barriers. However, there exists in the art, other modifications to partially or completely overcome the problem of nucleic acid secondary structures, including, for example, modifying the annealing conditions.

Third, the target sequence and/or propagating oligonucleotide from the translator conversion can have other kinetic barriers, for example, heavy crosstalk with the loops (or bulges) of gain1 or gain2 components, or with the free excess restriction oligonucleotides (see below; see, also, FIG. 6). The term "cross-talk" denotes an obfuscation or obscuring of a signal due, for example, to any undesired binding or complementary base pairing between two domains. Cross-talk can be overcome with careful design of domains and oligonucleotides.

High false positive rates tend to decrease the reliability of the detector; because a single free (unbound) propagating oligonucleotide can trigger the amplification system. Spontaneous release of a free propagating oligonucleotide is a Poisson process. In an ideal amplification system, there are zero occurrences during a given length of time (the observation window).

False positives can also occur for other reasons. First, if the stoichiometry of any of the gain2 components is more than about 2:1 of propagating to damping oligonucleotides, then there will be free single propagating oligonucleotides that can trigger amplification, regardless of whether there is a target sequence present. Thus, the stoichiometric ratio should be maintained slightly less than about 2:1.

Second, a correctly-formed gain2 component depends upon domain length and salt conditions. Under such conditions, a spontaneous complete dissociation, releasing a free propagating oligonucleotide may occur. One way to overcome spontaneous dissociation is increasing the domain lengths of the oligonucleotides, decreasing reaction temperatures, and/or increasing salt concentrations. In general, increasing hybridization between binding domains is more energetically favorable.

Third, since all hybridized oligonucleotides breath at some finite rate (which is dependent upon temperature and buffer conditions), it is possible that two correctly-formed gain2 components will contact each other while both are breathing. This form of false positive cannot be completely eliminated, but can be minimized by decreasing reaction temperatures, increasing salt concentrations, and decreasing component concentrations.

Macroscopic fluorescent changes (or signal) detected after passage of the observation window generally are not counted as "yes" or positive responses. Increasing the value of the observation window time tends to decrease false negative rates, while at the same time increasing false positive rates. In contrast, decreasing the observation window time tends to increase false negative rates while at the same time decrease false positive rates.

The kinetics of certain reactions must be fast enough so that the observation window is practical for that application (e.g., less than about one day), and slow enough for a reasonable observation window (e.g., longer than about one minute). Observation windows of between about one minute to about 24 hours span about 3 orders of magnitude. As such, sufficient allowance is provided such that a proper observation window can be defined, allowing for acceptable levels of both false negative and false positive results.

EXAMPLE 10

Restriction Oligonucleotides Restrict Hybridization of Propagating and Damping Oligonucleotide Incomplete components (i.e. P1*D3, P2*D1 and P3*D2) are involved in various fast reactions (13) to (18) below.

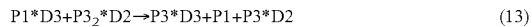
$$P1*D3 + P3_2*D2 \rightarrow P3*D3 + P1 + P3*D2 \quad (13)$$

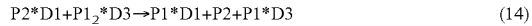
$$P2*D1 + P1_2*D3 \rightarrow P1*D1 + P2 + P1*D3 \quad (14)$$

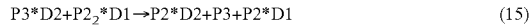
$$P3*D2 + P2_2*D1 \rightarrow P2*D2 + P3 + P2*D1 \quad (15)$$

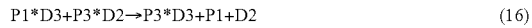
$$P1*D3 + P3*D2 \rightarrow P3*D3 + P1 + D2 \quad (16)$$

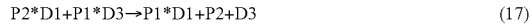
$$P2*D1 + P1*D3 \rightarrow P1*D1 + P2 + D3 \quad (17)$$

$$P3*D2 + P2*D1 \rightarrow P2*D2 + P3 + D1 \quad (18)$$

In reactions (13) to (18), the unhybridized propagating binding domains of the damping oligonucleotides of incomplete gain2 components (i.e. P1*D3, P2*D1 and P3*D2) can react with another propagating oligonucleotide as in reactions (10), (11) and (12), or can react with complete gain2 components (i.e. P1$_2$*D3, P2$_2$*D1 and P3$_2$*D2) as in reactions (13)-(18) above.

The products of reactions (13) to (18) are a two oligonucleotide complexes and one propagating oligonucleotide. For example, in reaction (13), incomplete gain2 component (P1*D3), reacts with a complete gain2 component (P3$_2$*D2), to produce a complementary two oligonucleotide complex (P3*D3), and one propagating oligonucleotide (P1) and another incomplete gain2 component (P3*D2). This reaction, and similar reactions (14) and (15), is relatively fast, since the complementary binding domains are sizeable (i.e. at least six nucleotides). In reactions (13), (14) and (15), the free propagating oligonucleotide(s) (P1, P2 and/or P3) can trigger the amplification system.

Similarly, two incomplete gain2 components (i.e. P1*D3, P2*D1 and P3*D2) can react with each other as shown in reactions (16), (17) and (18). For example, in reaction (16), two incomplete gain2 components (P1*D3 and P3*D2) react to form a complementary, inert, two-oligonucleotide complex (P3*D3) and one free propagating oligonucleotide (P1), and one free damping oligonucleotide (D2). The free propagating oligonucleotide (P1) can trigger the amplification system. The free damping oligonucleotide (D2) can bind to its substantially complementary oligonucleotide (P2) and form an inert two oligonucleotide complex (P2*D2). Similarly, depending on oligonucleotide design, the free damping oligonucleotide (D2) can also hybridize to a complementary target sequence.

Figure 6:
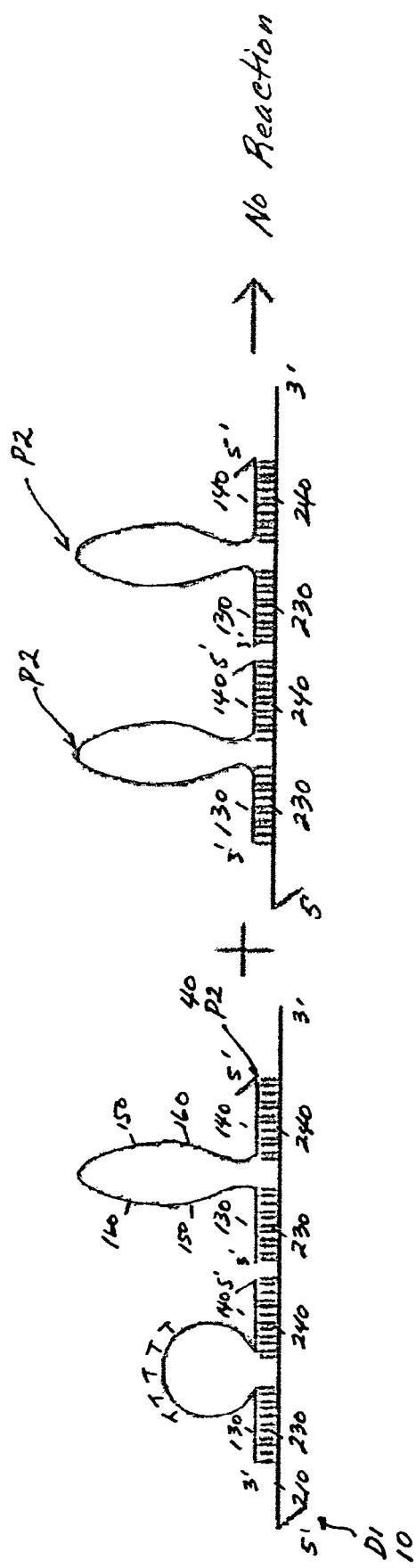
FIG. 6 illustrates the binding of a restriction oligonucleotide to one set of propagating oligonucleotide binding domains of a damping oligonucleotide.

To prevent reactions (13) to (18), restriction oligonucleotides are added to the solution containing the target sequence, the translator and the amplification system (see FIG. 6, left). Restriction oligonucleotides restrict the hybridizing ability of the free, unhybridized binding domains of the damping oligonucleotide. There is one restriction oligonucleotide per propagating oligonucleotide of a type (P1, P2 and/or P3). Each restriction oligonucleotide possesses two binding domains that flank a nonreactive domain (e.g., poly-T; see FIG. 6). Restriction oligonucleotides are named R1, R2, etc., such that Rn and Pn have identical 5' and 3' binding domains. After preparing, for example, gain2 components in roughly 1.98:1 ratio, excess restriction oligonucleotides are added to hybridize to all free and/or partially-free damping oligonucleotides.

Although, excess restriction oligonucleotides should be unreactive with properly-formed gain 2 components and free propagating oligonucleotides, this is not the case, as the binding domains of the restriction oligonucleotides can be complementary to the exposed toeholds of the properly formed components. As a result, exponential amplification of a propagating oligonucleotide which truly triggers the amplification system would be very slow kinetically due to the lack of available toeholds.

EXAMPLE 11

Toehold Domain Length and Location are Variable

Any of the domain sequences of the various oligonucleotides can be varied in length, including the toehold domain. Yurke et al. studied the effects of length of toeholds with regards to how they increase the kinetics of the branch migration process(es). See Yurke et al., supra. Yurke et al. showed that toeholds of 10 or more base pairs caused maximum rate increases, and that, intermediate values (2, 4, 6, 8 bp) showed progressive improvements on kinetics over the lack of a toehold. On the other hand, an oligonucleotide with only the toehold domain, but not the binding domains, such as a restriction oligonucleotide, stays hybridized only to the toehold domain for a duration whose natural log of length is proportional to the number of base pairs in the toehold (e.g. 5 base pairs stick n times longer than 4, and 6 sticks n times longer than 5).

Toehold domains greater than about 20 to 40 base pairs have hybridization energies that are slow, and tend to be irreversible. In one embodiment, a toehold of about 5 to 6 base pairs is sufficient. Restriction oligonucleotides can have altered binding domains so that they lack the base pairs complementary to the toehold domain of the damping oligonucleotides' toehold region. In addition to the hybridization of restriction oligonucleotides, there are also expected occasional hybridization between loops (or bulges) and toeholds of different gain2 components.

The 5' end, or 3' end, or both 5' and 3' ends, of a damping oligonucleotide can contain a toehold domain. The toeholds can be truncated (e.g., $A_t$, $E_t$ & $C_t$; see Table III, below) such that the entire damping oligonucleotide is substantially shorter in length than the entire length of the propagating oligonucleotide: (4x+5 bp) in length as opposed to (6x), where x is a defined domain length in base pairs.

EXAMPLE 12

Oligonucleotide Sequence Design

Domains of propagating and damping oligonucleotides can be arbitrary, however, there are some considerations, and guidelines are provided herein. First, all domains should have similar hybridization energies such that they will have similar melting temperatures. This objective can be met, for example, by designing the oligonucleotides such that all of the domains have about the same length. Methods for determining the melting temperature of an oligonucleotide are well known (see, e.g., Sambrook et al., supra, 1989).

Second, longer domain lengths decrease false positive rates, because the binding energy of each domain is increased, so that the probability of spontaneous dissociation (within the observation window) is decreased. Third, because branch migration in essence is a random-walk process, the reaction kinetics decreases with increased domain lengths. Fourth, longer domain lengths have increased cross-talk, which in turn, adversely affects both kinetics and error rates.

EXAMPLE 13

Minimization of Cross-Talk

Although cross-talk can obfuscate a signal due to unwanted binding or complementary base pairing between two domains, it can be overcome with careful design of domains and oligonucleotides. There are two main types of crosstalk—intramolecular and intermolecular reactions. Intramolecular crosstalk is the more problematic of the two reactions, because significant secondary structure in the propagating oligonucleotides greatly slows down the kinetics of reactions (1), (2) and (3); and can cause the formation of different dimers of propagating oligonucleotides.

In contrast, intermolecular cross-talk is of two main types: propagating-propagating, and propagating-damping. An example of the propagating-propagating type occurs when a propagating oligonucleotide (i.e. P1) spuriously hybridizes with another propagating oligonucleotide (i.e. P2) to form P1*P2. An example of propagating-damping type is a propagating oligonucleotide (i.e. P1) spuriously hybridizing with a damping oligonucleotide (i.e. D2) to form P1*D2. Propagating-propagating cross-talk is the more concerning of the two types, because once the amplification is triggered, there is expected to be large quantities of free propagating oligonucleotides, whereas excess damping oligonucleotides are few to start with.

Further, all propagating oligonucleotides are designed using only three of the four base-pairs. For example, use of adenine (A), thymine (T), and cytosine (C) for propagating oligonucleotides, and by complementarity, only T, A, and guanine (G) will be present for damping oligonucleotides.

EXAMPLE 14

Multiple Bulges to Induce Gain

The use of nucleic acid complexes with at least one loop (or bulge) or multiple loops has not previously been explored. As disclosed herein, oligonucleotides with bulges can be used to allow for signal gain in an integer stoichiometric ratio (e.g., 2:1), for example, gain2 components of the amplification system. Furthermore, the use of metastable structures to produce "gain" of single-oligonucleotide signals also has not been previously accomplished.

Any gain1 component can convert an input target sequence into a different output propagating oligonucleotide at a stoichiometric 1:1 ratio as long as there is enough time for the reaction to proceed to completion, and the output oligonucleotide is not being depleted by another reaction. Similarly, any gain2 component, will convert the input target sequence to an output propagating oligonucleotide at a 2:1, and so on.

EXAMPLE 15

Amplification System Components with Heterogeneous Inputs and Outputs

Components do not necessarily need to possess homogenous output oligonucleotides, or dissociated propagating oligonucleotides. For example, consider the following amplification system as described in reactions (19), (20) and (21) below:

$$PX + P2*P3*DX \rightarrow PX*DX + P2 + P3 \quad (19)$$

$$P2 + PX*D2 \rightarrow P2*D2 + PX \quad (20)$$

$$P3 + PX*D3 \rightarrow P3*D3 + PX \quad (21)$$

In reaction (19), the gain2 component (P2*P3*DX) includes two different propagating oligonucleotide (P2 and P3). When considered with respect to the above described oligonucleotides, the damping oligonucleotide (DX) in reaction (19) can be considered a hybrid oligonucleotide containing domains that are identical, in part, to D1 and D2, as discussed above, and complementary to P2 and P3 flanking domains. Similarly, in reaction (19), propagating oligonucleotide (PX) is a hybrid oligonucleotide containing sequences identical, in part, to P2 and P3; PX is substantially complementary to DX.

For example, in the above reaction (19), the DX damping oligonucleotide comprises 5' Tx-230-240-250-260-Ty 3'. One part of the DX damping oligonucleotide contains at least two propagating binding domains 230 and 240, which are complementary to the P2 propagating oligonucleotide domains 130 and 140. The other part of the DX damping oligonucleotide contains at least two propagating binding domains 250 and 260, which are complementary to the P3 propagating oligonucleotide domains 150 and 160. Hence, the DX damping oligonucleotide contains heterogeneous propagating binding domains. Also, while it takes only the propagating oligonucleotide (PX) to trigger the gain2 amplifier (P2*P3*DX), the propagating oligonucleotide (PX) is derived from two different components as shown in reactions (20) and (21).

EXAMPLE 16

Modification of Kinetics of the Reaction by Sequence Mismatches and Non-Binding Domains Various nucleotide mismatches can be introduced into the oligonucleotides to increase or decrease the rate of the kinetics of the exponential amplification. For example, a gain2 component can contain a mismatch in the binding domains of the propagating oligonucleotides. A substantially complementary propagating oligonucleotide containing no mismatches at the binding domains can later displace the propagating oligonucleotide with the mismatches by branch migration and hybridize to the damping oligonucleotide. Mismatches have a tendency to increase the rate of kinetics. In contrast, nucleotide mismatches between the triggering propagating oligonucleotide and the damping oligonucleotide of a gain2 component has a tendency to slow down the rate of kinetics.

Any number of non-binding domains can be inserted into the damping oligonucleotide. For example, a non-binding domain can be inserted into the damping oligonucleotide in the middle of the four propagating oligonucleotides binding domains of a gain2 component. In this scenario, a triggering propagating oligonucleotide hybridizes to the toehold of the damping oligonucleotide and displaces the first propagating oligonucleotide from the gain2 component with increased kinetics. However, displacement of the second propagating oligonucleotide is delayed because of the non-binding region on the damping oligonucleotide, which has to be bridged in order branch migration to continue.

The domains of oligonucleotides used to exemplify the compositions of the invention are shown in Table II. The letter "P" indicates "propagating oligonucleotide" and the letter "D" indicates "damping oligonucleotide". The numbers in the column to the left of the oligonucleotides, P or D, differentiate one propagating and/or damping oligonucleotide from the other. Propagating oligonucleotides (P) are in the 3' to 5' orientation and damping oligonucleotides (D) are in the opposite, or 5' to 3' direction. The binding domains are numbered to show complementarity of binding domains (e.g., domain 130 of P1 20 binds to domain 230 of the D1 10).

TABLE II

Oligonucleotide Domains

| No. | Oligo | Domain Sequence | Code | Code |
|---|---|---|---|---|
| 20 | P1 | 3' 110-130-140-130-140-120 5' | A = 110 | A* = 210 |
| 40 | P2 | 3' 130-150-160-150-160-140 5' | B = 120 | B* = 220 |
| 60 | P3 | 3' 150-11O-120-110-120-160 5' | C = 130 | C* = 230 |
| 10 | D1 | 5' 210-230-240-230-240-210 3' | D = 140 | D* = 240 |
| 30 | D2 | 5' 230-250-260-250-260-230 3' | E = 150 | E* = 250 |
| 50 | D3 | 5' 250-210-220-210-220-250 3' | F = 160 | F* = 260 |

Table III provides a listing of the nucleotide sequences for the above-mentioned domains in Table II. "Code" indicates the letters that, when compared to the Code in Table II, identify the numerical equivalent of the domain. Number in parentheses is SEQ ID NO:. All nucleotide sequences are written in the 5' to 3' direction.

TABLE III

| Code | Nucleotide Sequence |
|---|---|
| A | ATCCCATCAATATCTTCTCA (1) |
| A* | TGAGAAGATATTGATGGGAT (2) |
| B | CTATCATACACACTCTACTA (3) |
| B* | TAGTAGAGTGTGTATGATAG (4) |
| C | TTCCACTACCTACACATCAA (5) |
| C* | TTGATGTGTAGGTAGTGGAA (6) |
| D | TAACCTCCTCTACAATCCTT (7) |
| D* | AAGGATTGTAGAGGAGGTTA (8) |
| E | AATACTTCTTCACTCAACAT (9) |
| E* | ATGTTGAGTGAAGAAGTATT (10) |
| F | TCTCCTACCCTTCATAACTA (11) |
| F* | TAGTTATGAAGGGTAGGAGA (12) |
| At | TGAGA (13) |
| Ct | TTGAT (14) |
| $E_t$ | ATGTT (15) |

Table IV shows a solute concentration useful for performing an amplification reaction.

TABLE IV

Solute and Solute Concentrations

| Molarity | Solute |
|---|---|
| 12.5 mM | $Mg(C_2H_3O_2)_2$ |
| 1.0 mM | EDTA |
| 40.0 mM | Tris |
| 20.0 mM | $HC_2H_3O_2$ |

Although the invention has been described with reference to the above example, it will be understood that modifications and variations are encompassed within the spirit and scope of the invention. Accordingly, the invention is limited only by the following claims.

---

What is claimed is:

1. An amplifier nucleic acid molecule 1, comprising:
a) a first damping oligonucleotide 10, which comprises, in operative linkage in a 5' to 3' orientation,
a first toehold domain 210 comprising at least two nucleotides, and
at least two first propagating oligonucleotide binding domains 230 and 240, each of binding domains 230 and 240 comprising at least six nucleotides; and
b) at least one first propagating oligonucleotide 40, which comprises, in operative linkage in a 3' to 5' orientation,
a first domain 130, which is complementary to and selectively hybridizes the first propagating oligonucleotide binding domain 230,
at least two sets of individual domains 150 and 160 arranged in alternating order, wherein each of domains 150 and 160 are not complementary to the first damping oligonucleotide 10, and wherein each domain 150 has an identical nucleic acid sequence and each domain 160 has an identical nucleic acid sequence, and wherein each of domains 150 and 160 have different nucleic acid sequences, and wherein each of domains 150 and 160 comprises at least six nucleotides, and
a sixth domain 140, which is complementary to and selectively hybridizes to the first propagating oligonucleotide binding domain 240,
wherein the amplifier nucleic acid molecule 1 comprises a complex comprising the first damping oligonucleotide 10 and the first propagating oligonucleotide 40, and wherein the nucleic acid molecule 1, the first damping oligonucleotide 10, and the first propagating oligonucleotide 40 do not comprise domains which are complementary or selectively hybridize to a target sequence to be identified by the complex.

2. The amplifier nucleic acid molecule 1 of claim 1, wherein the first damping oligonucleotide 10 comprises four first propagating oligonucleotide binding domains 230, 240, 230 and 240,
wherein the amplifier nucleic acid molecule 1 comprises two first propagating oligonucleotides 40,
said amplifier nucleic acid molecule 1 comprising a complex comprising the first damping oligonucleotide 10 and the two first propagating oligonucleotides 40.

3. The amplifier nucleic acid molecule 1 of claim 1, wherein the first damping oligonucleotide 10 comprises six first propagating oligonucleotide binding domains 230, 240, 230, 240, 230, and 240,
wherein the amplifier nucleic acid molecule 1 comprises three first propagating oligonucleotides 40,
said amplifier nucleic acid molecule 1 comprising a complex comprising the first damping oligonucleotide 10 and the three first propagating oligonucleotides 40.

4. The amplifier nucleic acid molecule 1 of claim 1, wherein the first damping oligonucleotide 10 further comprises a 3' terminal nucleotide sequence domain 220.

5. The amplifier nucleic acid molecule 1 of claim 1, wherein the first propagating oligonucleotide 40 further comprises a label.

6. The amplifier nucleic acid molecule 1 of claim 5, wherein the first propagating oligonucleotide 40 further comprises a fluorescence quencher, which quenches fluorescence of the fluorescent label.

7. The amplifier nucleic acid molecule 1 of claim 1, wherein the first damping oligonucleotide 10 further comprises a fluorescence quencher, which quenches fluorescence of the fluorescent label.

8. A composition, comprising:
the amplifier nucleic acid molecule of claim 1; and
a restriction oligonucleotide, which comprises, operatively linked and in a 3' to 5' orientation, a first domain 130, a seventh domain, which is not complementary to damping oligonucleotide 10, wherein the seventh domain consists of poly d(T), poly d(G, and poly d(C) residues, and a sixth domain 140, wherein the restriction oligonucleotide selectively hybridizes to the damping oligonucleotide.

9. An amplifier nucleic acid molecule 1, comprising:
a) a first damping oligonucleotide 10, which comprises, in operative linkage in a 5' to 3' orientation,
a first toehold domain 210 comprising at least two nucleotides, and
four first propagating oligonucleotide binding domains 230, 240, 230 and 240, each of binding domains 230, 240, 230 and 240 comprising at least six nucleotides; and
b) two first propagating oligonucleotides 40, each of which comprises, in operative linkage in a 3' to 5' orientation,
a first domain 130, which is complementary to and selectively hybridizes to the first propagating oligonucleotide binding domain 230,
at least two sets of individual domains 150 and 160 arranged in alternating order, wherein each of domains 150 and 160 are not complementary to the first damping oligonucleotide 10, and wherein each domain 150 has an identical nucleic acid sequence and each domain 160 has an identical nucleic acid sequence, and wherein each of domains 150 and 160 have different nucleic acid sequences, and wherein each of domains 150 and 160 comprises at least six nucleotides, and, a sixth domain 140, which is complementary to and selectively hybridizes to the first propagating oligonucleotide binding domain 240 of the damping oligonucleotide 10, wherein the first domain 130 and sixth domain 140 of each first propagating oligonucleotide 40 selectively hybridize to the damping oligonucleotide 10, wherein the amplifier nucleic acid molecule 1 comprises a complex comprising the first damping oligonucleotide 10 and the two first propagating oligonucleotides 40, and wherein the nucleic acid molecule 1, the first damping oligonucleotide 10, and the first propagating oligonucleotide 40 do not comprise domains which are complementary or selectively hybridize to a target sequence to be identified by the complex.

10. A target nucleic acid molecule translator system, comprising a first gain1 component 4 and a second gain1 component 5, a) the first gain1 component 4, comprising
   i) a fourth damping oligonucleotide 70, comprising, in operative linkage in a 5' to 3' orientation,
      a first toehold domain 26, which comprises at least two nucleotides and is complementary to and selectively hybridizes to a 3' nucleotide sequence of the target nucleic acid molecule; and
      two fourth propagating oligonucleotide binding domains 280 and 290, each comprising at least six nucleotides; and
   ii) a fourth propagating oligonucleotide 80 comprising, in operative linkage in a 3' to 5' orientation,
      a first domain 180, which is complementary to and selectively hybridizes to the fourth propagating oligonucleotide binding domain 280,
      two domains 110 and 120, which are not complementary to the fourth damping oligonucleotide 70, wherein each domain of the fourth propagating oligonucleotide 80 selectively hybridizes and is complementary to one or more domains contained in a fifth damping oligonucleotide 90, and wherein each of domains 110 and 120 comprising at least six nucleotides, and
      a fourth domain 190, which is complementary to and selectively hybridizes to the fourth propagating oligonucleotide binding domain 290,
   wherein the first gain1 component 4 comprises a complex of the fourth damping oligonucleotide 70 and the fourth propagating oligonucleotide 80; and b) the second gain1 component 5, comprising
   i) a fifth damping oligonucleotide 90, comprising, in operative linkage in a 5' to 3' orientation,
      a first toehold domain 280, which is complementary to and selectively hybridizes to the first domain 180 of the fourth propagating oligonucleotide 80,
      two third propagating oligonucleotide binding domains 210 and 220, each comprising at least six nucleotides, and
      a fourth domain 290,
      wherein said fifth damping oligonucleotide 90 is complementary to and selectively hybridize to said fourth propagating oligonucleotide 80; and ii) a third propagating oligonucleotide 20, which comprises, in operative linkage in a 3' to 5' orientation,
      a first domain 110, which is complementary to and selectively hybridizes to third propagating oligonucleotide binding domain 210,
      at least two sets of individual domains 130 and 140 arranged in alternating order, wherein each of domains 130 and 140 are not complementary to the fifth damping oligonucleotide 90, and wherein each domain 130 has an identical nucleic acid sequence and each domain 140 has an identical nucleic acid sequence, and wherein each of domains 130 and 140 have different nucleic acid sequences, and wherein each of domains 130 and 140 comprises at least six nucleotides, and
      a sixth domain 120, which is complementary to and selectively hybridizes to third propagating oligonucleotide binding domain 220,
   wherein the second gain1 component 5 comprises a complex of the fifth damping oligonucleotide 90 and the third propagating oligonucleotide 20, and wherein the third propagating oligonucleotide 20 does not comprise domains which selectively hybridize to a target sequence to be identified by the system.

11. A nucleic acid amplification system, comprising:
a) the first amplifier nucleic acid amplifier 1 as set forth in claim 9,
b) a second amplifier nucleic acid molecule 2, comprising
   i) a second damping oligonucleotide 30, which comprises, in operative linkage in a 5' to 3' orientation,
      a first toehold domain 230 comprising at least two nucleotides, and
      at least four second propagating oligonucleotide binding domains 250, 260, 250, and 260, each of which comprises at least six nucleotides,
      wherein the second damping oligonucleotide 30 is complementary to and can selectively hybridize to the first propagating oligonucleotide 40; and
   ii) two second propagating oligonucleotides 60, each of which comprises, in operative linkage in a 3' to 5' orientation,
      a first domain 150, which is complementary to and selectively hybridizes to the second propagating oligonucleotide binding domain 250,
      at least four domains 110, 120, 110, and 120, which are not substantially complementary to the second damping oligonucleotide 30, each of domains 110, 120, 110, and 120 comprising at least six nucleotides, and
      a sixth domain 160, which is complementary to and selectively hybridizes to the second propagating oligonucleotide binding domain 260;
   wherein the amplifier nucleic acid molecule 2 comprises a complex comprising the second damping oligonucleotide 30 and the two second propagating oligonucleotides 60; and c) a third amplifier nucleic acid molecule 3, comprising
   i) a third damping oligonucleotide 50, which comprises, in operative linkage in a 5' to 3' orientation,
      a first toehold domain 250 comprising at least two nucleotides, and
      at least four second propagating oligonucleotide binding domains 210, 220, 210, and 220, each of which comprises at least six nucleotides,
      wherein the third damping oligonucleotide 50 is complementary to and can selectively hybridize to the second propagating oligonucleotide 60; and ii) two third propagating oligonucleotides 20, each of which comprises, in operative linkage in a 3' to 5' orientation,
- a first domain 110, which is complementary to and selectively hybridizes to the second propagating oligonucleotide binding domain 210,
- at least four domains 130, 140, 130, and 140, which are not substantially complementary to the second damping oligonucleotide 50, each of domains 130, 140, 130, and 140 comprising at least six nucleotides, and
- a sixth domain 120, which is complementary to and selectively hybridizes to the second propagating oligonucleotide binding domain 220,
- wherein the third propagating oligonucleotide 20 is complementary to and can selectively hybridize to the first damping oligonucleotide 10, and wherein the amplifier nucleic acid molecule 3 comprises a complex comprising the second damping oligonucleotide 50 and the two second propagating oligonucleotides 20.

12. The nucleic acid amplification system of claim 11, further comprising the target nucleic acid molecule translator system of claim 10.

13. The nucleic acid amplification system of claim 11, wherein the amplifier nucleic acid molecule 1, the amplifier nucleic acid molecule 2, the amplifier nucleic acid molecule 3, or a combination thereof further comprises a label.

14. The nucleic acid amplification system of claim 13, wherein the label comprises a fluorescence resonance energy transfer (FRET) pair.

15. A method of identifying a target nucleic acid molecule in a sample, comprising
contacting at least one sample with the nucleic acid amplification system of claim 12, under conditions suitable for selective hybridization of the target nucleic acid molecule to the first toehold domain 26 of the damping oligonucleotide 70 of the first gain1 component 4 of the target nucleic acid molecule translator system, and
detecting dissociation of a propagating oligonucleotide from an amplifier nucleic acid molecule selected from
the first propagating oligonucleotide 60 from the amplifier nucleic acid molecule 1,
the second propagating oligonucleotide 40 from the amplifier nucleic acid molecule 2,
the third propagating oligonucleotide 20 from the amplifier nucleic acid molecule 3,
and a combination thereof,
wherein increased dissociation of the propagating oligonucleotide from the amplifier nucleic acid molecule in the presence of the target nucleic acid molecule as compared to the absence of the target nucleic acid molecule is indicative of the presence of a target nucleic acid molecule, thereby identifying the target nucleic acid molecule in the sample.

16. The method of claim 15, wherein the sample comprises a biological sample or an environmental sample.

17. A method of identifying an agent that effects expression of a target nucleic acid molecule, comprising
a) contacting a sample comprising the target nucleic acid molecule with a test agent under conditions suitable for effecting expression of the target nucleic acid molecule;
b) further contacting the sample with the nucleic acid amplification system of claim 12, under conditions suitable for selective hybridization of the target nucleic acid molecule to the first toehold domain 26 of the damping oligonucleotide 70 of the first gain1 component 4 of the target nucleic acid molecule translator system, and
c) detecting dissociation of a propagating oligonucleotide from an amplifier nucleic acid molecule selected from
the first propagating oligonucleotide 60 from the amplifier nucleic acid molecule 1,
the second propagating oligonucleotide 40 from the amplifier nucleic acid molecule 2,
the third propagating oligonucleotide 20 from the amplifier nucleic acid molecule 3,
and a combination thereof,
wherein a change in dissociation of the propagating oligonucleotide from the amplifier nucleic acid molecule in the presence of the test agent as compared to the absence of the test agent identifies the test agent as an agent that effects expression of the target nucleic acid molecule.

18. The method of claim 17, which is performed in a high throughput format.

19. A method of translating a target nucleic acid molecule into a propagating oligonucleotide, which can initiate amplification of a nucleic acid amplification system under isothermal conditions, comprising:
contacting a sample comprising a target nucleic acid molecule with the target nucleic acid molecule translator of claim 10 under conditions suitable for selective hybridization of the target nucleic acid molecule to the toehold domain 26 of the damping oligonucleotide 70 of the first gain1 component 4 of the target nucleic acid molecule translator system,
wherein the target nucleic acid molecule hybridizes to the damping oligonucleotide 70 by branch migration and displaces the fourth propagating oligonucleotide 80 from the first gain1 component 4, thereby generating a dissociated fourth propagating oligonucleotide 80, and
wherein the first domain 180 of the dissociated fourth propagating oligonucleotide 80 selectively hybridizes to the first toehold domain 280 of the fifth damping oligonucleotide 90 of the second gain1 component 5,
wherein the dissociated fourth propagating oligonucleotide 80 selectively hybridizes to the fifth damping oligonucleotide 90 by branch migration and displaces the third propagating oligonucleotide 20, thereby generating a dissociated second propagating oligonucleotide 20, which can initiate amplification of a nucleic acid amplification system under isothermal conditions.

20. The method of claim 19, wherein the dissociated propagating oligonucleotide 20 is stoichiometric with respect to the target nucleic acid molecule in the sample.

21. The method of claim 19, further comprising initiating amplification of a nucleic acid amplification system, said method comprising contacting, under isothermal conditions, a target nucleic acid molecule and the target nucleic acid molecule translator with the nucleic acid amplification system of claim 11, whereby the dissociated second propagating oligonucleotide 20 selectively hybridizes to the first toehold domain 210 of the first damping oligonucleotide 10, thereby initiating amplification of the nucleic acid amplification system.

* * * * *